(12) United States Patent
Green

(10) Patent No.: US 7,531,556 B2
(45) Date of Patent: May 12, 2009

(54) COMPOSITIONS USEFUL AS INHIBITORS OF ROCK AND OTHER PROTEIN KINASES

(75) Inventor: Jeremy Green, Waltham, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 454 days.

(21) Appl. No.: 11/115,661

(22) Filed: Apr. 27, 2005

(65) Prior Publication Data

US 2006/0019956 A1 Jan. 26, 2006

Related U.S. Application Data

(60) Provisional application No. 60/565,879, filed on Apr. 28, 2004.

(51) Int. Cl.
*C07D 403/04* (2006.01)
*C07D 413/02* (2006.01)
*A61K 31/415* (2006.01)
*A61K 31/4196* (2006.01)
*A61K 31/4245* (2006.01)
*A61P 3/10* (2006.01)
*A61P 11/06* (2006.01)
*A61P 27/06* (2006.01)
*A61P 27/14* (2006.01)

(52) U.S. Cl. .................. 514/336; 546/268.7; 546/269.7
(58) Field of Classification Search ............... 546/268.7, 546/269.7; 514/336
See application file for complete search history.

(56) References Cited

U.S. PATENT DOCUMENTS

2004/0023989 A1* 2/2004 Fryburg et al. ........... 514/262.1

FOREIGN PATENT DOCUMENTS

| WO | WO 02/14311 A2 | 2/2002 |
|----|----|----|
| WO | WO 02/46184 A1 | 6/2002 |
| WO | WO 02/064586 A2 | 8/2002 |
| WO | WO 02/092573 A2 | 11/2002 |
| WO | WO 03/091246 A1 | 11/2003 |
| WO | WO 2004/016597 A2 | 2/2004 |
| WO | WO 2004/083203 A1 | 9/2004 |

OTHER PUBLICATIONS

Mass, R. D., Int. J. Radiation Oncology Bio. Phys.vol. 58(3): 932-940, 2004.*
Fabbro et al. Pharmacology & therapeutics 93, 79-98, 2002.*
Cecil Textbook of Medicine, edited by Bennet, J.C., and Plum F., 20th edition,vol. 1, 1004-1010, 1996.*
Udupi et al., Indian Journal of Heterocyclic Chemistry, 9(4), 283-286; CAPLUS Abstract: CA 134: 131502, 2000.*

* cited by examiner

*Primary Examiner*—Venkataraman Balasubramanian
(74) *Attorney, Agent, or Firm*—Daniel A. Pearson

(57) ABSTRACT

The present invention relates to compounds useful as inhibitors of protein kinases. The invention also provides pharmaceutically acceptable compositions comprising said compounds and methods of using the compositions in the treatment of various disease, conditions, or disorders.

8 Claims, No Drawings

COMPOSITIONS USEFUL AS INHIBITORS OF ROCK AND OTHER PROTEIN KINASES

CROSS REFERENCE TO RELATED APPLICATIONS

This application claims priority to U.S. Provisional Patent Application 60/565,879 filed Apr. 28, 2004, the entire contents of which are hereby incorporated herein by reference.

FIELD OF INVENTION

The present invention relates to compounds useful as inhibitors of protein kinases. The invention also provides pharmaceutically acceptable compositions comprising the compounds of the invention and methods of using the compositions in the treatment of various disorders.

BACKGROUND OF THE INVENTION

The search for new therapeutic agents has been greatly aided in recent years by a better understanding of the structure of enzymes and other biomolecules associated with diseases. One important class of enzymes that has been the subject of extensive study is protein kinases.

Protein kinases constitute a large family of structurally related enzymes that are responsible for the control of a variety of signal transduction processes within the cell. (See, Hardie, G. and Hanks, S. *The Protein Kinase Facts Book, I and II*, Academic Press, San Diego, Calif.: 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids, etc.). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al., *Cell* 1992, 70, 419-429; Kunz et al., *Cell* 1993, 73, 585-596; Garcia-Bustos et al., *EMBO J.* 1994, 13, 2352-2361).

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies and asthma, Alzheimer's disease and hormone-related diseases. Accordingly, there has been a substantial effort in medicinal chemistry to find protein kinase inhibitors that are effective as therapeutic agents.

ROCK Protein Kinase

One kinase family of interest is Rho-associated coiled-coil forming protein serine/threonine kinase (ROCK), which is believed to be an effector of Ras-related small GTPase Rho. The ROCK family includes p160ROCK (ROCK-1) (Ishizaki et al., *EMBO J.* 1996, 15, 1885-1893) and ROKα/Rho-kinase/ROCK-II (Leung et al., *J. Biol. Chem.* 1995, 270, 29051-29054; Matsui et al., *EMBO J.* 1996, 15, 2208-2216; Nakagawa et al., *FEBS Lett.* 1996, 392, 189-193), protein kinase PKN (Amano et al., *Science* 1996, 271, 648-650; Watanabe et al., *Science* 1996, 271, 645-648), and citron and citron kinase (Madaule et al. *Nature*, 1998, 394, 491-494; Madaule et al., *FEBS Lett.* 1995, 377, 243-248). The ROCK family of kinases have been shown to be involved in a variety of functions including Rho-induced formation of actin stress fibers and focal adhesions (Leung et al., *Mol. Cell Biol.* 1996, 16, 5313-5327; Amano et al., *Science,* 1997, 275, 1308-1311; Ishizaki et al., *FEBS Lett.* 1997, 404, 118-124) and in down-regulation of myosin phosphatase (Kimura et al., *Science,* 1996, 273, 245-248), platelet activation (Klages et al., *J. Cell. Biol.*, 1999, 144, 745-754), aortic smooth muscle contraction by various stimuli (Fu et al., *FEBS Lett.*, 1998, 440, 183-187), thrombin-induced responses of aortic smooth muscle cells (Seasholtz et al., *Cir. Res.,* 1999, 84, 1186-1193), hypertrophy of cardiomyocytes (Kuwahara et al., *FEBS Lett.,* 1999, 452, 314-318), bronchial smooth muscle contraction (Yoshii et al., *Am. J. Respir. Cell Mol. Biol.,* 1999, 20, 1190-1200), smooth muscle contraction and cytoskeletal reorganization of non-muscle cells (Fukata et al., *Trends in Pharm. Sci* 2001, 22, 32-39), activation of volume-regulated anion channels (Nilius et al., *J. Physiol.,* 1999, 516, 67-74), neurite retraction (Hirose et al., *J. Cell. Biol.*, 1998, 141, 1625-1636), neutrophil chemotaxis (Niggli, *FEBS Lett.,* 1999, 445, 69-72), wound healing (Nobes and Hall, *J. Cell. Biol.,* 1999, 144, 1235-1244), tumor invasion (Itoh et al., *Nat. Med.,* 1999, 5, 221-225) and cell transformation (Sahai et al., *Curr. Biol.,* 1999, 9, 136-145).

More specifically, ROCK has been implicated in various diseases and disorders including hypertension (Satoh et al., *J. Clin. Invest.* 1994, 94, 1397-1403; Mukai et al., *FASEB J.* 2001, 15, 1062-1064; Uehata et al., *Nature* 1997, 389, 990-994; Masumoto et al., *Hypertension,* 2001, 38, 1307-1310), cerebral vasospasm (Sato et al., *Circ. Res.* 2000, 87, 195-200; Miyagi et al., *J. Neurosurg.* 2000, 93, 471-476; Tachibana et al., *Acta Neurochir (Wien)* 1999, 141, 13-19), coronary vasospasm (Shimokawa et al., *Jpn. Cir. J.* 2000, 64, 1-12; Kandabashi et al., *Circulation* 2000, 101, 1319-1323; Katsumata et al., *Circulation* 1997, 96, 4357-4363; Shimokawa et al., *Cardiovasc. Res.* 2001, 51, 169-177; Utsunomiya et al., *J. Pharmacol.* 2001, 134, 1724-1730; Masumoto et al., *Circulation* 2002, 105, 1545-1547), bronchial asthma (Chiba et al., *Comp. Biochem. Physiol. C Pharmacol. Toxicol. Endocrinol.* 1995, 11, 351-357; Chiba et al., *Br. J. Pharmacol.* 1999, 127, 597-600; Chiba et al., *Br. J. Pharmacol.* 2001, 133, 886-890; Iizuka et al., *Eur. J. Pharmacol.* 2000, 406, 273-279), preterm labor (Niro et al., *Biochem. Biophys. Res. Commun.* 1997, 230, 356-359; Tahara et al., *Endocrinology* 2002, 143, 920-929; Kupittayanant et al., *Pflugers Arch.* 2001, 443, 112-114), erectile dysfunction (Chitaley et al., *Nat. Med.* 2001, 7, 119-122; Mills et al., *J. Appl. Physiol.* 2001, 91, 1269-1273), glaucoma (Honjo et al., *Arch. Ophthalmol.* 2001, 1171-1178; Rao et al., *Invest. Ophthalmol. Vis. Sci.* 2001, 42, 1029-1037), vascular smooth muscle cell proliferation (Shimokawa et al., *Cardiovasc. Res.* 2001, 51, 169-177; Morishige et al., *Arterioscler. Thromb. Vasc. Biol.* 2001, 21, 548-554; Eto et al., *Am. J. Physiol. Heart Circ. Physiol.* 2000, 278, H1744-H1750; Sawada et al., *Circulation* 2000, 101, 2030-2023; Shibata et al., *Circulation* 2001, 103, 284-289), myocardial hypertrophy (Hoshijima et al., *J. Biol. Chem.* 1998, 273, 7725-77230; Sah et al., *J. Biol. Chem.* 1996, 271, 31185-31190; Kuwahara et al., *FEBS Lett.* 1999, 452, 314-318; Yanazume et al., *J. Biol. Chem.* 2002, 277, 8618-8625), malignoma (Itoh et al., *Nat. Med.* 1999, 5, 221-225; Genda et al., *Hepatology* 1999, 30, 1027-1036; Somlyo et al., *Biochem. Biophys. Res. Commun.* 2000, 269, 652-659), ischemia/reperfusion-induced injury (Ikeda et al., *J. of Surgical Res.* 2003, 109, 155-160; Miznuma et al. *Transplantation* 2003, 75, 579-586), endothelial dysfunction (Hernandez-Perera et al., *Circ. Res.* 2000, 87, 616-622; Laufs et al., *J. Biol. Chem.* 1998, 273, 24266-24271; Eto et al., *Circ. Res.* 2001, 89, 583-590), Crohn's Disease and colitis (Segain et al. *Gastroenterology* 2003, 124(5), 1180-1187), neurite outgrowth (Fournier et al.

J. Neurosci. 2003, 23, 1416-1423), Raynaud's Disease (Shimokawa et al. J. Cardiovasc. Pharmacol. 2002, 39, 319-327), angina (Utsunomiya et al. Br. J. Pharmacol. 2001, 134, 1724-1730; Masumoto et al, Circulation 2002, 105, 1545-1547; Shimokawa et al, J. Cardiovasc. Pharmacol., 2002, 40, 751-761; Satoh et al., Jpn. J. Pharmacol., 2001, 87, 34-40), Alzheimer's disease (Zhou et al., Science 2003, 302, 1215-1218), benign prostatic hyperplasia (Rees et al., J. Urology, 2003, 170, 2517-2522), and atherosclerosis (Retzer et al. FEBS Lett. 2000, 466, 70-74; Ishibashi et al. Biochim. Biophys. Acta 2002, 1590, 123-130). Accordingly, the development of inhibitors of ROCK kinase would be useful as therapeutic agents for the treatment of disorders implicated in the ROCK kinase pathway.

ERK Protein Kinase

ERK2 (extracellular signal regulated kinase) is a member of the mammalian mitogen-activated protein (MAP) 1 kinase family. (MAP) 1 kinases are serine/threonine kinases that mediate intracellular signal transduction pathways (Cobb and Goldsmith, J Biol. Chem., 1995, 270, 14843; Davis, Mol. Reprod. Dev. 1995, 42, 459) and are activated by mitogens and growth factors (Bokemeyer et al., Kidney Int. 1996, 49, 1187). Members of the MAP kinase family share sequence similarity and conserved structural domains, and, in addition to ERK2, include the JNK (Jun N-terminal kinase), and p38 kinases. JNKs and p38 kinases are activated in response to the pro-inflammatory cytokines TNF-alpha and interleukin-1, and by cellular stress such as heat shock, hyperosmolarity, ultraviolet radiation, lipopolysaccharides and inhibitors of protein synthesis (Derijard et al., Cell 1994, 76, 1025; Han et al., Science 1994, 265, 808; Raingeaud et al., J Biol. Chem. 1995, 270, 7420; Shapiro and Dinarello, Proc. Natl. Acad. Sci. USA 1995, 92, 12230). In contrast, ERKs are activated by mitogens and growth factors (Bokemeyer et al., Kidney Int. 1996, 49, 1187).

ERK2 is a widely distributed protein kinase that achieves maximum activity when both Thr183 and Tyr185 are phosphorylated by the upstream MAP kinase, MEK1 (Anderson et al., Nature 1990, 343, 651; Crews et al., Science 1992, 258, 478). Upon activation, ERK2 phosphorylates many regulatory proteins, including the protein kinases Rsk90 (Bjorbaek et al., J. Biol. Chem. 1995, 270, 18848) and MAPKAP2 (Rouse et al., Cell 1994, 78, 1027), and transcription factors such as ATF2 (Raingeaud et al., Mol. Cell Biol. 1996, 16, 1247), Elk-1 (Raingeaud et al., Mol. Cell Biol. 1996, 16, 1247), c-Fos (Chen et al., Proc. Natl. Acad. Sci. USA 1993, 90, 10952), and c-Myc (Oliver et al., Proc. Soc. Exp. Biol. Med. 1995, 210, 162). ERK2 is also a downstream target of the Ras/Raf dependent pathways (Moodie et al., Science 1993, 260, 1658) and may help relay the signals from these potentially oncogenic proteins. ERK2 has been shown to play a role in the negative growth control of breast cancer cells (Frey and Mulder, Cancer Res. 1993, 57, 628) and hyperexpression of ERK2 in human breast cancer has been reported (Sivaraman et al., J Clin. Invest. 1997, 99, 1478). Activated ERK2 has also been implicated in the proliferation of endothelin-stimulated airway smooth muscle cells, suggesting a role for this kinase in asthma (Whelchel et al., Am. J. Respir. Cell Mol. Biol. 1997, 16, 589).

GSK-3 Protein Kinase

Glycogen synthase kinase-3 (GSK-3) is a serine/threonine protein kinase comprised of α and β isoforms that are each encoded by distinct genes [Coghlan et al., Chemistry & Biology 2000, 7, 793-803; and Kim and Kimmel, Curr. Opinion Genetics Dev., 2000 10, 508-514]. GSK-3 has been implicated in various diseases including diabetes, Alzheimer's disease, CNS disorders such as manic depressive disorder and neurodegenerative diseases, and cardiomyocyte hypertrophy [PCT Application Nos.: WO 99/65897 and WO 00/38675; and Haq et al., J. Cell Biol. 2000, 151, 117-130]. These diseases are associated with the abnormal operation of certain cell signaling pathways in which GSK-3 plays a role. GSK-3 has been found to phosphorylate and modulate the activity of a number of regulatory proteins. These proteins include glycogen synthase, which is the rate limiting enzyme necessary for glycogen synthesis, the microtubule associated protein Tau, the gene transcription factor β-catenin, the translation initiation factor e1F2B, as well as ATP citrate lyase, axin, heat shock factor-1, c-Jun, c-myc, c-myb, CREB, and CEPBα. These diverse protein targets implicate GSK-3 in many aspects of cellular metabolism, proliferation, differentiation, and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., PNAS 1996, 93, 8455-8459; Cross et al., Biochem. J. 1994, 303, 21-26); Cohen, Biochem. Soc. Trans. 1993, 21, 555-567; and Massillon et al., Biochem J. 1994, 299, 123-128]. However, in a diabetic patient, where the insulin response is impaired, glycogen synthesis and glucose uptake fail to increase despite the presence of relatively high blood levels of insulin. This leads to abnormally high blood levels of glucose with acute and long-term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [see, PCT Application: WO 00/38675]. Therapeutic inhibitors of GSK-3 are therefore potentially useful for treating diabetic patients suffering from an impaired response to insulin.

GSK-3 activity is also associated with Alzheimer's disease. This disease is characterized by the well-known β-amyloid peptide and the formation of intracellular neurofibrillary tangles. Aβ peptides are derived from the amyloid precursor protein (APP) by sequential proteolysis, catalysed by the aspartyl protease BACE2, followed by presenilin-dependent γ-secretase cleavage. It has been demonstrated that antibodies against β-amyloid plaques can slow cognitive decline in patients with Alzheimer's disease (Hock et al., Neuron, 2003, 38, 547-554), and thus other β-amyloid-lowering strategies (e.g., the development of agents capable of inhibiting β-amyloid peptide) would be useful in the treatment of Alzheimer's disease and other psychotic and neurodegenerative disorders. Additionally, the neurofibrillary tangles contain hyperphosphorylated Tau protein, in which Tau is phosphorylated on abnormal sites, and thus agents capble of inhibiting the hyperphosphorylation of Tau protein would be useful in the treatment of Alzherimer's disease and other psychotic and neurodegenerative disorders.

GSK-3 is known to phosphorylate these abnormal sites in cell and animal models. Furthermore, inhibition of GSK-3 has been shown to prevent hyperphosphorylation of Tau in cells [Lovestone et al., Current Biology 1994, 4, 1077-86; and Brownlees et al., Neuroreport 1997, 8, 3251-55]. Therefore, GSK-3 activity promotes generation of the neurofibrillary tangles and the progression of Alzheimer's disease. It has also been shown that GSK-3 facilitates APP processing and that a GSK-3 inhibitor (lithium) inhibits of the generation of Aβ peptides through the inhibition of GSK-3 (Phiel et al. *Nature* 2003, 423, 435-439). Thus, the development of inhibitors of GSK-3 would be useful for the reduction of the formation of amyloid plaques and neurofibrillry tangles, the pathological hallmarks of Alzheimer's Disease, and would also be useful for the treatment of other psychotic and neurodegenerative disorders.

Another substrate of GSK-3 is β-catenin, which is degradated after phosphorylation by GSK-3. Reduced levels of β-catenin have been reported in schizophrenic patients and have also been associated with other diseases related to increase in neuronal cell death [Zhong et al., *Nature* 1998, 395, 698-702; Takashima et al., *PNAS* 1993, 90, 7789-93; and Pei et al., *J. Neuropathol. Exp* 1997, 56, 70-78].

GSK-3 activity is also associated with stroke [Wang et al., *Brain Res* 2000, 859, 381-5; Sasaki et al., *Neurol Res* 2001, 23, 588-92; Hashimoto et al., *J. Biol. Chem* 2002, 277, 32985-32991].

AGC-Family of Protein Kinases

The AGC sub-family of kinases phosphorylate their substrates at serine and threonine residues and participate in a variety of well-known signaling processes, including, but not limited to cyclic AMP signaling, the response to insulin, apoptosis protection, diacylglycerol signaling, and control of protein translation (Peterson et al., *Curr. Biol.* 1999, 9, R521). This sub-family includes PKA, PKB (c-Akt), PKC, PRK1, 2, $p70^{S6K}$, SGK1, and PDK.

AKT Protein Kinase

AKT (also known as PKB or Rac-PK beta), a serine/threonine protein kinase, has been shown to be overexpressed in several types of cancer and is a mediator of normal cell functions [(Khwaja, A., *Nature* 1999, 401, 33-34); (Yuan, Z. Q., et al., *Oncogene* 2000, 19, 2324-2330); (Namikawa, K., et al., *J Neurosci.* 2000, 20, 2875-2886,)]. AKT comprises an N-terminal pleckstrin homology (PH) domain, a kinase domain and a C-terminal "tail" region. Three isoforms of human AKT kinase (AKT-1, -2 and -3) have been reported so far [(Cheng, J. Q., *Proc. Natl. Acad. Sci. USA* 1992, 89, 9267-9271); (Brodbeck, D. et al., *J. Biol. Chem.* 1999, 274, 9133-9136)]. The PH domain binds 3-phosphoinositides, which are synthesized by phosphatidyl inositol 3-kinase (PI3K) upon stimulation by growth factors such as platelet derived growth factor (PDGF), nerve growth factor (NGF) and insulin-like growth factor (IGF-1) [(Kulik et al., *Mol. Cell. Biol.*, 1997, 17, 1595-1606,); (Hemmings, B. A., *Science*, 1997, 275, 628-630)]. Lipid binding to the PH domain promotes translocation of AKT to the plasma membrane and facilitates phosphorylation by another PH-domain-containing protein kinases, PDK1 at Thr308, Thr309, and Thr305 for the AKT isoforms 1, 2 and 3, respectively. A second, as of yet unknown, kinase is required for the phosphorylation of Ser473, Ser474 or Ser472 in the C-terminal tails of AKT-1, -2 and -3 respectively, in order to yield a fully activated AKT enzyme.

Once localized to the membrane, AKT mediates several functions within the cell including the metabolic effects of insulin (Calera, M. R. et al., *J. Biol. Chem.* 1998, 273, 7201-7204) induction of differentiation and/or proliferation, protein synthesis and stress responses (Alessi, D. R. et al., *Curr. Opin. Genet. Dev.* 1998, 8, 55-62,).

Manifestations of altered AKT regulation appear in both injury and disease, the most important role being in cancer. The first account of AKT was in association with human ovarian carcinomas where expression of AKT was found to be amplified in 15% of cases (Cheng, J. Q. et al., *Proc. Natl. Acad. Sci. U.S.A.* 1992, 89, 9267-9271). It has also been found to be overexpressed in 12% of pancreatic cancers (Cheng, J. Q. et al., *Proc. Natl. Acad. Sci. U.S.A.* 1996, 93, 3636-3641). It was demonstrated that AKT-2 was over-expressed in 12% of ovarian carcinomas and that amplification of AKT was especially frequent in 50% of undifferentiated tumours, suggesting that AKT may also be associated with tumour aggressiveness (Bellacosa, et al., *Int. J. Cancer* 1995, 64, 280-285).

Increased levels of PI3K pathway activity has been directly associated with the development of a number of human cancers, progression to an aggressive refractory state (acquired resistance to chemotherapies) and poor prognosis. This increased activity has been attributed to a series of key events including decreased activity of negative pathway regulators such as the phosphatase PTEN, activating mutations of positive pathway regulators such as Ras, and overexpression of components of the pathway itself such as AKT, examples include: brain (gliomas), breast, colon, head and neck, kidney, lung, liver, melanoma, ovarian, pancreatic, prostate, sarcoma, thyroid [(Teng, D. H. et al., *Cancer Res.,* 1997 57, 5221-5225), (Brognard, J. et al., *Cancer Res.,* 2001, 61, 3986-3997), (Cheng, J. Q. et al., *Proc. Natl. Acad. Sci.* 1996, 93, 3636-3641), (*Int. J. Cancer* 1995, 64, 280), (Graff, J. R., *Expert Opin. Ther. Targets* 2002, 6, 103-113), (*Am. J. Pathol.* 2001, 159, 431)].

Additionally, decreased pathway function through gene knockout, gene knockdown, dominant negative studies, and small molecule inhibitors of the pathway have been demonstrated to reverse many of the cancer phenotypes in vitro (some studies have also demonstrated a similar effect in vivo) such as block proliferation, reduce viability and sensitize cancer cells to known chemotherapies in a series of cell lines, representing the following cancers: pancreatic [(Cheng, J. Q. et al., *Proc. Natl. Acad. Sci.* 1996, 93, 3636-3641), (*Neoplasia* 2001, 3, 278)], lung [(Brognard, J. et al., *Cancer Res.* 2001, 61, 3986-3997), (*Neoplasia* 2001, 3, 278)], ovarian [(Hayakawa, J. et al., *Cancer Res.* 2000, 60, 5988-5994), (*Neoplasia* 2001, 3, 278)], breast (*Mol. Cancer Ther.* 2002, 1, 707), colon [(*Neoplasia* 2001, 3, 278), (Arico, S. et al., *J. Biol. Chem.* 2002, 277, 27613-27621)], cervical (*Neoplasia* 2001, 3, 278), prostate [(*Endocrinology* 2001, 142, 4795), (Thakkar, H. et al. *J. Biol. Chem.* 2001, 276, 38361-38369), (Chen, X. et al., *Oncogene* 2001, 20, 6073-6083)] and brain (glioblastomas) [(Flynn, P. et al., *Curr. Biol.* 2000, 10, 1439-1442)].

PKA Protein Kinase

PKA (also known as cAMP-dependent protein kinase) has been shown to regulate many vital functions including energy metabolism, gene transcription, proliferation, differentiation, reproductive function, secretion, neuronal activity, memory, contractility and motility (Beebe, S. J., *Semin. Cancer Biol.* 1994, 5, 285-294). PKA is a tetrameric holoenzyme, which contains two catalytic subunits bound to a homo-dimeric regulatory subunit (which acts to inhibit the catalytic subunits). On binding of cAMP (enzyme activation), the catalytic subunits dissociate from the regulatory subunits to yield the active serine/threonine kinase (McKnight, G. S. et al., *Recent Prog. Horm. Res.* 1988, 44, pp. 307). Three isoforms of the catalytic subunit (C-α, C-β and C-γ) have been reported to date (Beebe, S. J. et al., *J. Biol. Chem.* 1992, 267, 25505-25512) with the C-α subunit being the most extensively studied, primarily because of its elevated expression in primary and metastatic melanomas (Becker, D. et al., *Oncogene* 1990, 5, 1133). To date, strategies to modulate the activity of the C-α subunit involve the use of antibodies, molecules that block PKA activity by targeting regulatory dimers and antisense oligonucleotides expression.

P70$^{S6K}$ Protein Kinase

The ribosomal protein kinases p70$^{S6K}$-1 and -2 are also members of the AGC sub-family of protein kinases and catalyze the phosphorylation and subsequent activation of the ribosomal protein S6, which has been implicated in the translational up-regulation of mRNAs coding for the components of the protein synthetic apparatus. These mRNAs contain an oligopyrimidine tract at their 5' transcriptional start site, termed a 5'TOP, which has been shown to be essential for their regulation at the translational level (Volarevic, S. et al., *Prog. Nucleic Acid Res. Mol. Biol.* 2001, 65, 101-186). p70$^{S6K}$ dependent S6 phosphorylation is stimulated in response to a variety of hormones and growth factors primarily via the PI3K pathway (Coffer, P. J. et al., *Biochem. Biophys. Res. Commun,* 1994 198, 780-786), which may be under the regulation of mTOR, since rapamycin acts to inhibit p70$^{S6K}$ activity and blocks protein synthesis, specifically as a result of a down-regulation of translation of these mRNA's encoding ribosomal proteins (Kuo, C. J. et al., *Nature* 1992, 358, 70-73).

SGK1 Protein Kinase

Serum- and glucocorticoid-induced protein kinase 1 (SGK1) is an ubiquitously expressed kinase. SGK1, together with the related kinases serum- and glucocorticoid-induced protein kinase 2 (SGK2) and serum- and glucocorticoid-induced protein kinase (SGK3), belongs to the AGC subfamily of protein kinases. The catalytic domain of SGK1 is 54% identical to that of Protein Kinase B (PKB also known as AKT) (Lang, F. and Cohen, P. *Sci STKE.* 2001 Nov. 13; 2001(108):RE17).

SGK1 is important for regulating Na+ homeostasis. It affects Na+ resorbtion by the amelioride-sensitive epithelial Na+ channels (ENaC) located in the distal renal tubal cells (Pearce D Trends Endocrinol Metab (2001) 12: 341-347). SGK1-deficient mice have decreased renal Na+ excretion during Na+ depletion (Wullf, P. et al. J Clin Invest (2002) 110:1263-1268) and its activity is relevant to hypertension in man (Busjahn, A. et al. Hypertension (2002) 40:256-260). SGK1 regulation of ENaC may also affect cell volume Bohmer, C., et al., *Cell Physiol Biochem.* (2000) 10:187-194).

SGK1 has a potential role in regulating cell survival through its phosphorylation of FKHRL1, a transcription factor involved in controlling apoptosis (Brunet, A. et al. *Mol Cell Biol (*2001) 21:952-65). It is also involved in regulation of potassium ion channels (Gamper N., et al. *Pflugers Arch* (2002) 445:60-66) and thus plays a role in cell survival and neuronal excitability.

PDK1 Protein Kinase

In vitro PDK1 catalyses the phosphorylation of Thr252 in the activation loop of the p70 catalytic domain, which is indispensable for p70 activity (Alessi, D. R., *Curr. Biol.,* 1998, 8, 69-81). The use of rapamycin and gene deletion studies of dp70S6K from *Drosophila* and p70$^{S6K}$1 from mouse have established the central role p70 plays in both cell growth and proliferation signaling.

The 3-phosphoinositide-dependent protein kinase-1 (PDK1) plays a key role in regulating the activity of a number of kinases belonging to the AGC subfamily of protein kinases (Alessi, D. et al., *Biochem. Soc. Trans* 2001, 29, 1). These include isoforms of protein kinase B (PKB, also known as AKT), p70 ribosomal S6 kinase (S6K) (Avruch, J. et al., *Prog. Mol. Subcell. Biol.* 2001, 26, 115), and p90 ribosomal S6 kinase (Frödin, M. et al., *EMBO J.* 2000, 19, 2924-2934). PDK1 mediated signaling is activated in response to insulin and growth factors and as a consequence of attachment of the cell to the extracellular matrix (integrin signaling). Once activated these enzymes mediate many diverse cellular events by phosphorylating key regulatory proteins that play important roles controlling processes such as cell survival, growth, proliferation and glucose regulation [(Lawlor, M. A. et al., *J. Cell Sci.* 2001, 114, 2903-2910), (Lawlor, M. A. et al., *EMBO J.* 2002, 21, 3728-3738)]. PDK1 is a 556 amino acid protein, with an N-terminal catalytic domain and a C-terminal pleckstrin homology (PH) domain, which activates its substrates by phosphorylating these kinases at their activation loop (Belham, C. et al., *Curr. Biol.* 1999, 9, R93-R96). Many human cancers including prostate and NSCL have elevated PDK1 signaling pathway function resulting from a number of distinct genetic events such as PTEN mutations or over-expression of certain key regulatory proteins [(Graff, J. R., *Expert Opin. Ther. Targets* 2002, 6, 103-113), (Brognard, J., et al., *Cancer Res.* 2001, 61, 3986-3997)]. Inhibition of PDK1 as a potential mechanism to treat cancer was demonstrated by transfection of a PTEN negative human cancer cell line (U87MG) with antisense oligonucleotides directed against PDK1. The resulting decrease in PDK1 protein levels led to a reduction in cellular proliferation and survival (Flynn, P., et al., *Curr. Biol.* 2000, 10, 1439-1442). Consequently the design of ATP binding site inhibitors of PDK1 offers, amongst other treatments, an attractive target for cancer chemotherapy.

The diverse range of cancer cell genotypes has been attributed to the manifestation of the following six essential alterations in cell physiology: self-sufficiency in growth signaling, evasion of apoptosis, insensitivity to growth-inhibitory signaling, limitless replicative potential, sustained angiogenesis, and tissue invasion leading to metastasis (Hanahan, D. et al., *Cell* 2000, 100, 57-70). PDK1 is a critical mediator of the PI3K signalling pathway, which regulates a multitude of cellular function including growth, proliferation and survival. Consequently, inhibition of this pathway could affect four or more of the six defining requirements for cancer progression. As such it is anticipated that a PDK1 inhibitor will have an effect on the growth of a very wide range of human cancers.

Accordingly, there is a great need to develop inhibitors of ROCK, ERK, GSK, and members of the AGC sub-family of protein kinases (e.g., PKA, PDK, p70$^{S6K}$-1 and -2, and AKT) that would be useful in treating various diseases or conditions associated with ROCK, ERK or GSK activation, or activation of the AGC sub-family of protein kinases (e.g., PKA, PDK, p70$^{S6K}$-1 and -2, and AKT), particularly given the inadequate treatments currently available for the majority of these disorders.

SUMMARY OF THE INVENTION

It has now been found that compounds of this invention, and pharmaceutically acceptable compositions thereof, are effective as inhibitors of ROCK, ERK, GSK, and members of the AGC sub-family of protein kinases (e.g., PKA, PDK, p70$^{S6K}$-1 and -2, and AKT). These compounds have the general formula I:

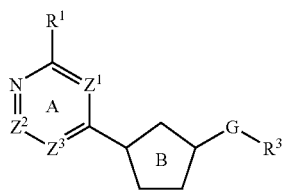

or a pharmaceutically acceptable salt thereof, wherein Ring B, $R^1$, $R^3$, $Z^1$, $Z^2$, $Z^3$, and G, are as defined below.

These compounds, and pharmaceutically acceptable compositions thereof, are useful for treating or lessening the severity of a variety of disorders, including allergic disorders such as asthma and atopic dermatitis, autoimmune diseases such as SLE lupus and psoriasis, conditions associated with organ transplantation, proliferative disorders such as cancer, inflammatory diseases, destructive bone disorders, hypertension, angina pectoris, cerebrovascular contraction, asthma, peripheral circulation disorder, premature birth, arteriosclerosis, spasm, retinopathy, erectile dysfunction (ED), Alzheimer's Disease, reperfusion/ischemia induced injury (e.g., stroke), and AIDS, to name a few.

The compounds provided by this invention are also useful for the study of kinases in biological and pathological phenomena; the study of intracellular signal transduction pathways mediated by such kinases, and the comparative evaluation of new kinase inhibitors.

DETAILED DESCRIPTION OF CERTAIN EMBODIMENTS OF THE INVENTION

I. General Description of Compounds of the Invention:

The present invention relates to a compound of formula I:

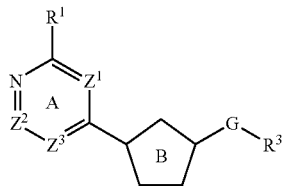

or a pharmaceutically acceptable salt thereof, wherein:

Ring B is a 5-membered heteroaryl ring selected from pyrazole, imidazole, triazole, tetrazole, furan, oxazole, isoxazole, or oxadiazole, wherein Ring B is optionally substituted with 0-3 $R^4$ groups;

$Z^1$ and $Z^3$ are each independently N or $CR^Z$, and $Z^2$ is N or $CR^1$, provided that $Z^2$ and $Z^3$ are not simultaneously N;

$R^Z$ is halogen, CN, $NO_2$, or $U_{(n)}R'$;

each $R^1$ is independently halogen, CN, $NO_2$, or $V_{(m)}R$;

V is an optionally substituted $C_{1-6}$ alkylidene chain, wherein up to two methylene units of the chain are optionally and independently replaced by —S—, —O—, —CS—, —$CO_2$—, —OC(O)—, —C(O)—, —C(O)C(O)—, —C(O)NR—, —$SO_2$NR—, —C(O)NRNR—, —OC(O)NR—, —S(O)—, —$SO_2$—, —P(O)—, —$PO_2$—, or —P(O)R—;

G is —$NR^2$-$Q^1$- or —C(O)—;

$Q^1$ is —C(O)—, —$SO_2$—, —C(O)NR—, or —$SO_2$NR—;

$R^2$ is $U_{(n)}R'$;

$R^3$ is $Q^2$-$Ar^1$, or $R^2$ and $Q^1$-$R^3$, taken together with the nitrogen atom, form the cyclic group:

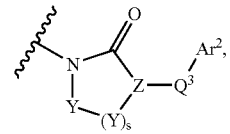

where s is 1 or 2, each occurrence of Y is independently, as valency and stability permit, —C(O)—, —CS—, —$SO_2$—, —O—, —S—, —$NR^5$—, or —$C(R^5)_2$—;

each occurrence of $R^4$ is independently halogen, CN, $NO_2$, or $U_{(n)}R$;

each occurrence of U is independently an optionally substituted $C_{1-6}$ alkylidene chain, wherein up to two methylene units of the chain are optionally and independently replaced by —NR—, —S—, —O—, —CS—, —$CO_2$—, —OC(O)—, —C(O)—, —C(O)C(O)—, —C(O)NR—, —NRC(O)—, —$NRCO_2$—, —$SO_2$NR—, —$NRSO_2$—, —C(O)NRNR—, —NRC(O)NR—, —OC(O)NR—, —NRNR—, —$NRSO_2$NR—, —S(O)—, —$SO_2$—, —P(O)—, —$PO_2$—, or —P(O)R—;

m and n are each independently 0 or 1;

each occurrence of R is independently hydrogen or an optionally substituted $C_{1-6}$ aliphatic group;

each occurrence of R' is independently hydrogen or an optionally substituted $C_{1-6}$ aliphatic group, a 3-8-membered saturated, partially unsaturated, or fully unsaturated monocyclic ring having 0-4 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or:

R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;

each $R^5$ is independently $U_{(n)}R'$;

$Q^2$ and $Q^3$ are each independently a valence bond or a $C_{1-6}$ alkylidene chain, wherein up to two methylene units of the chain are each optionally and independently replaced by —NR'—, —S—, —O—, —CS—, —$CO_2$—, —OC(O)—, —C(O)—, —C(O)C(O)—, —C(O)NR'—, —NR'C(O)—, —$NR'CO_2$—, —$SO_2$NR'—, —$NR'SO_2$—, —C(O)NR'NR'—, —NR'C(O)NR'—, —OC(O)NR'—, —NR'NR'—, —$NR'SO_2NR'$—, —S(O)—, —$SO_2$—, —P(O)—, —$PO_2$—, or —P(O)R'—; and wherein any carbon atom in the one or more methylene units is optionally substituted with one or two occurrences of $R^6$, each occurrence of $R^6$ is independently halogen, CN, $NO_2$, or $U_{(n)}R'$, or:

two occurrences of $R^6$, or R' and $R^6$, taken together with the atoms to which they are bound, form an optionally substituted 3-6-membered cycloalkyl, heterocyclyl, aryl or heteroaryl ring;

Ar$^1$ and Ar$^2$ are each independently a 5-8 membered saturated, partially unsaturated, or fully unsaturated monocyclic ring having 0-4 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein Ar$^1$ and Ar$^2$ are each optionally and independently substituted with 0-5 occurrences of TR$^7$;

T is a valence bond or is a C$_1$-C$_6$ alkylidene chain wherein up to two methylene units of T are optionally and independently replaced by —NR—, —S—, —O—, —CS—, —CO$_2$—, —OC(O)—, —C(O)—, —C(O)C(O)—, —C(O)NR—, —NRC(O)—, —NRCO$_2$—, —SO$_2$NR—, —NRSO$_2$—, —C(O)NRNR—, —NRC(O)NR—, —OC(O)NR—, —NRNR—, —NRSO$_2$NR—, —S(O)—, —SO$_2$—, —P(O)—, —PO$_2$—, or —P(O)R—; and each occurrence of R$^7$ is independently R', halogen, NO$_2$, or CN.

2. Compounds and Definitions:

Compounds of this invention include those described generally above, and are further illustrated by the embodiments, sub-embodiments, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic C$_3$-C$_8$ hydrocarbon or bicyclic C$_8$-C$_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members is an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroaralkoxy and the like) group may contain one or more substituents. Suitable substituents on the unsaturated carbon atom of an aryl or heteroaryl group are selected from halogen; R°; OR°; SR°; 1,2-methylene-dioxy; 1,2-ethylenedioxy; phenyl (Ph) optionally substituted with R°; —O(Ph) optionally substituted with R°; $(CH_2)_{1-2}$(Ph), optionally substituted with R°; CH=CH(Ph), optionally substituted with R°; $NO_2$; CN; $N(R°)_2$; NR°C(O)R°; $NR°C(O)N(R°)_2$; $NR°CO_2R°$; —NR°NR°C(O)R°; $NR°NR°C(O)N(R°)_2$; $NR°NR°CO_2R°$; C(O)C(O)R°; $C(O)CH_2C(O)R°$; $CO_2R°$; C(O)R°; $C(O)N(R°)_2$; $OC(O)N(R°)_2$; $S(O)_2R°$; $SO_2N(R°)_2$; S(O)R°; $NR°SO_2N(R°)_2$; $NR°SO_2R°$; $C(=S)N(R°)_2$; C(=NH)—$N(R°)_2$; or $(CH_2)_{0-2}NHC(O)R°$ wherein each independent occurrence of R° is selected from hydrogen, optionally substituted $C_{1-6}$ aliphatic, an unsubstituted 5-6 membered heteroaryl or heterocyclic ring, phenyl, O(Ph), or $CH_2$(Ph), or, notwithstanding the definition above, two independent occurrences of R°, on the same substituent or different substituents, taken together with the atom(s) to which each R° group is bound, form a 3-8 membered cycloalkyl, heterocyclyl, aryl, or heteroaryl ring having 0-4 heteroatoms independently selected from nitrogen, oxygen, or sulfur. Optional substituents on the aliphatic group of R° are selected from $NH_2$, $NH(C_{1-4}$aliphatic), $N(C_{1-4}$aliphatic$)_2$, halogen, $C_{1-4}$aliphatic, OH, $O(C_{1-4}$aliphatic), $NO_2$, CN, $CO_2H$, $CO_2(C_{1-4}$aliphatic), $O(haloC_{1-4}$ aliphatic), or halo$C_{1-4}$aliphatic, wherein each of the foregoing $C_{1-4}$aliphatic groups of R° is unsubstituted.

An aliphatic or heteroaliphatic group or a non-aromatic heterocyclic ring may contain one or more substituents. Suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, $=NN(R*)_2$, =NNHC(O)R*, $=NNHCO_2$(alkyl), $=NNHSO_2$(alkyl), or =NR*, where each R* is independently selected from hydrogen or an optionally substituted $C_{1-6}$ aliphatic. Optional substituents on the aliphatic group of R* are selected from $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), wherein each of the foregoing $C_{1-4}$aliphatic groups of R* is unsubstituted.

Optional substituents on the nitrogen of a non-aromatic heterocyclic ring are selected from $R^+$, $N(R^+)_2$, $C(O)R^+$, $CO_2R^+$, $C(O)C(O)R^+$, $C(O)CH_2C(O)R^+$, $SO_2R^+$, $SO_2N(R^+)_2$, $C(=S)N(R^+)_2$, C(=NH)—$N(R^+)_2$, or $NR^+SO_2R^+$; wherein $R^+$ is hydrogen, an optionally substituted $C_{1-6}$ aliphatic, optionally substituted phenyl, optionally substituted O(Ph), optionally substituted $CH_2$(Ph), optionally substituted $(CH_2)_{1-2}$(Ph); optionally substituted CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form a 3-8-membered cycloalkyl, heterocyclyl, aryl, or heteroaryl ring having 0-4 heteroatoms independently selected from nitrogen, oxygen, or sulfur. Optional substituents on the aliphatic group or the phenyl ring of $R^+$ are selected from $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), wherein each of the foregoing $C_{1-4}$aliphatic groups of $R^+$ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R° (or $R^+$, or any other variable similarly defined herein), are taken together with the atom(s) to which each variable is bound to form a 3-8-membered cycloalkyl, heterocyclyl, aryl, or heteroaryl ring having 0-4 heteroatoms independently selected from nitrogen, oxygen, or sulfur. Exemplary rings that are formed when two independent occurrences of R° (or $R^+$, or any other variable similarly defined herein) are taken together with the atom(s) to which each variable is bound include, but are not limited to the following: a) two independent occurrences of R° (or $R^+$, or any other variable similarly defined herein) that are bound to the same atom and are taken together with that atom to form a ring, for example, $N(R°)_2$, where both occurrences of R° are taken together with the nitrogen atom to form a piperidin-1-yl, piperazin-1-yl, or morpholin-4-yl group; and b) two independent occurrences of R° (or $R^+$, or any other variable similarly defined herein) that are bound to different atoms and are taken together with both of those atoms to form a ring, for example where a phenyl group is substituted with two occurrences of OR°

these two occurrences of R° are taken together with the oxygen atoms to which they are bound to form a fused 6-membered oxygen containing ring:

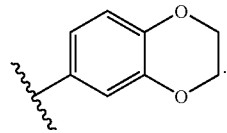

It will be appreciated that a variety of other rings can be formed when two independent occurrences of R° (or $R^+$, or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmuetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C— or $^{14}$C-enriched carbon are within the scope of this invention. Such compounds are useful, for example, as analytical tools or probes in biological assays.

3. Description of Exemplary Compounds:

In general, for compounds of formula I each occurrence of $R^1$ is independently halogen, CN, NO$_2$, or V$_{(m)}$R, and each occurrence of $R^Z$ is independently halogen, CN, NO$_2$, or U$_{(n)}$R'. In certain embodiments, the $R^1$ group of formula I is hydrogen, halogen, optionally substituted —C$_1$-C$_4$aliphatic, —OH, —OR, or —SR. In other embodiments $R^1$ groups are hydrogen, halogen, —CH$_3$, —CH$_2$CH$_3$, —OH, —OCH$_3$, or —SCH$_3$.

Exemplary $R^Z$ groups of formula I are each independently hydrogen, halogen, C$_1$-C$_4$aliphatic, OH, OR', or N(R)(R'). In certain embodiments, $R^Z$ groups are each independently hydrogen, halogen, Me, OH, OMe, NH$_2$, or N(CH$_3$)$_2$.

According to one embodiment, the $R^1$ group of formula I is hydrogen.

According to another embodiment, the $R^Z$ group of formula I is hydrogen.

As described generally above, Ring B is a 5-membered heteroaryl ring selected from pyrazole, imidazole, triazole, tetrazole, faran, oxazole, isoxazole, or oxadiazole, wherein Ring B is optionally substituted with 0-3 $R^4$ groups. According to one embodiment, Ring B is triazole, imidazole, or oxadiazole wherein said Ring B is optionally substituted with 0-2 $R^4$ groups.

According to another embodiment, the present invention provides a compound of formula I wherein Ring B is selected from any of the following:

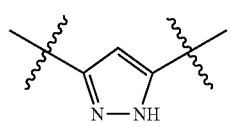

i

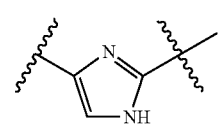

ii

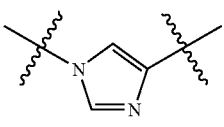

iii

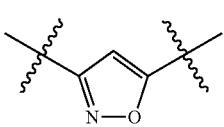

iv

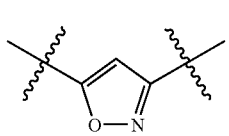

v

-continued

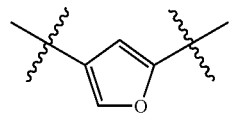

vi

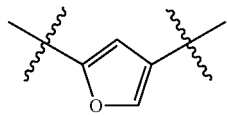

vii

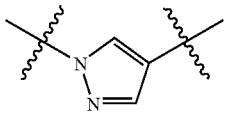

viii

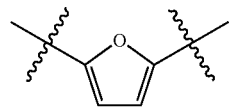

ix

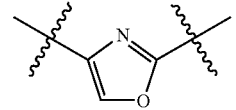

x

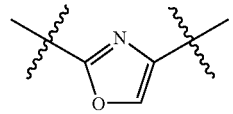

xi

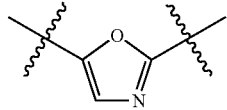

xii

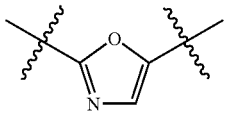

xiii

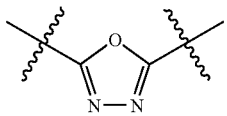

xiv

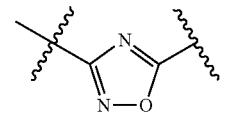

xv

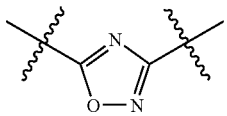

xvi

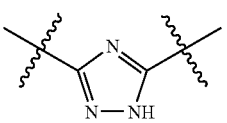

xvii

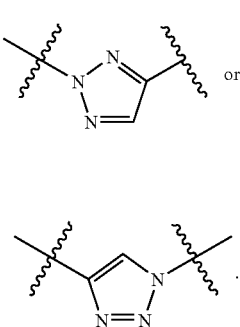

xviii

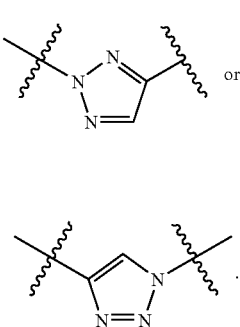

xiv

In certain embodiments, Ring B is oxadiazole.

In other embodiments, Ring B is imidazole optionally substituted with 0-2 $R^4$ groups.

In yet other embodiments, Ring B is triazole optionally substituted with 0-1 $R^4$ group.

As described generally above, each Ring B moiety of formula I is optionally and independently substituted with zero, one or two occurrences of $R^4$, as valency permits, wherein each occurrence of $R^4$ is independently halogen, CN, $NO_2$, or $U_{(n)}R$. In some embodiments, each $R^4$ group is independently hydrogen, $C_{1-6}$aliphatic, —CN, —C(O)R, —C(O)OR, —C(O)N(R)$_2$, or halogen.

In certain embodiments, G is —$NR^2$-$Q^1$- and $R^3$ is $Q^2$-$Ar^1$. Accordingly, another aspect of the present invention relates to a compound of formula II:

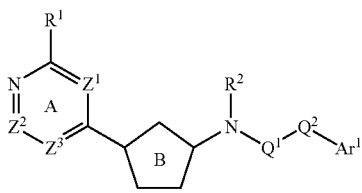

II or a pharmaceutically acceptable salt thereof, wherein $R^1$, $Z^1$, $Z^2$, $Z^3$, Ring B, $R^2$, $Q^1$, $Q^2$, and $Ar^1$ are as defined generally and in classes and subclasses above and herein.

In other embodiments, G is —C(O)— and $R^3$ is $Q^2$-$Ar^1$. Accordingly, yet another aspect of the present invention relates to a compound of formula III:

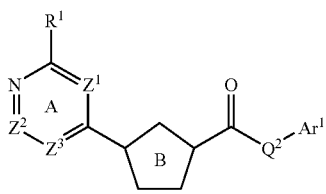

III or a pharmaceutically acceptable salt thereof, wherein $R^1$, $Z^1$, $Z^2$, $Z^3$, Ring B, $Q^2$, and $Ar^1$ are as defined generally and in classes and subclasses above and herein.

In certain embodiments, the present invention relates to a compound of formula I or II wherein $R^2$ is hydrogen.

In general, for compounds of formulae I and II, and subsets thereof, $R^2$ is $U_{(n)}R'$. In certain embodiments, $R^2$ is $U_{(n)}R'$, wherein n is 1, and U is a $C_{1-6}$ alkylidene chain wherein one or two methylene units of U are optionally and independently replaced by —O—, —NR—, —S—, or —C(O)—. According to one embodiment, R and R' are taken together with the nitrogen atom to which they are bound, form an optionally substituted 5- or 6-membered saturated, partially unsaturated, or unsaturated heterocyclyl ring. According to another embodiment, U is —$CH_2$—, —$CH_2CH_2$—, —$CH_2CH_2CH_2$—, —$CH_2CH_2CH_2CH_2$—, —$CH_2O$—, —$CH_2S$—, —$CH_2NR$—, —$CH_2CH_2O$—, —$CH_2CH_2S$—, —$CH_2CH_2NR$—, —$CH_2CH_2CH_2O$—, —$CH_2CH_2CH_2S$—, —$CH_2CH_2CH_2NR$—, —$CH_2CH_2CH_2CH_2O$—, —$CH_2CH_2CH_2CH_2S$—, —$CH_2CH_2CH_2CH_2NR$—, —$CH_2CH_2OCH_2CH_2$—, —$(CH_2)_4NHCH_2$—, —$(CH_2)_3NHCH_2CH_2$—, or —$CH_2CH_2NHCH_2CH_2$—. Exemplary R' groups include hydrogen, $C_1$-$C_4$alkyl, an optionally substituted group selected from tetrahydropyranyl, pyrrolidinyl, piperidinyl, piperazinyl, morpholinyl, thiomorpholinyl, pyridinyl, imidazolyl, phenyl, or cyclohexyl.

As described generally above, for compounds of formula I, and subsets thereof, $Q^1$ is —C(O)—, —$SO_2$—, —$NR^2$—, —$NR^2C(O)$—, —C(O)$NR^2$—, or —$SO_2NR^2$—. In some embodiments, $Q^1$ is —C(O)—, —C(O)$NR^2$—, —$NR^2$—, —$SO_2$—, or —$SO_2NR^2$—. In other embodiments, $Q^1$ is —C(O)—, —$NR^2$—, or —C(O)$NR^2$—.

For compounds of general formula I, and subsets thereof, $Q^2$ is a valence bond or a $C_{1-6}$ alkylidene chain, wherein up to two methylene units of the chain are each optionally and independently replaced by —NR'—, —S—, —O—, —CS—, —$CO_2$—, —OC(O)—, —C(O)—, —C(O)C(O)—, —C(O)NR'—, —NR'C(O)—, —NR'$CO_2$—, —$SO_2NR'$—, —NR'$SO_2$—, —C(O)NR'NR'—, —NR'C(O)NR'—, —OC(O)NR'—, —NR'NR'—, —NR'$SO_2NR'$—, —S(O)—, —$SO_2$—, —P(O)—, —$PO_2$—, or —P(O)R'—; and wherein any carbon atom in the one or more methylene units is optionally substituted with one or two occurrences of $R^6$, wherein each occurrence of $R^6$ is independently halogen, CN, $NO_2$, or $U_nR'$, or two occurrences of $R^6$, or R' and $R^6$, taken together with the atoms to which they are bound, form an optionally substituted 3-6-membered cycloalkyl, heterocyclyl, aryl or heteroaryl ring.

In some embodiments, $Q^2$ is a direct bond, or is —$(CHR^6)_q$—, —$(CHR^6)_qO$—, —$(CHR^6)_qS$—, —$(CHR^6)_qS(O)_2$—, —$(CHR^6)_qS(O)$—, —$(CHR^6)_qNR$—, or —$CHR^6)_qC(O)$—, wherein each q is independently 0, 1, 2, or 3. In certain other embodiments, $R^6$ is R', —N(R)(R'), —$(CH_2)_{1-4}N(R)(R')$, —$(CH_2)_{1-4}C(CH_3)_2N(R)(R')$, —OR', —$(CH_2)_{1-4}OR'$, —$NR(CH_2)_{1-4}N(R)(R')$, —$NR(CH_2)_{1-4}SO_2R'$, —$NR(CH_2)_{1-4}C(O)OR'$, or —$NR(CH_2)_{1-4}C(O)R'$, or two occurrences of $R^6$, taken together with the atoms to which they are bound, form an optionally substituted 3-6-membered saturated, partially unsaturated, or fully unsaturated ring. Examples of such $R^6$ groups include, but are not limited to —$CH_2OH$, —$CH_2CH_2OH$, —OH, —OMe, —OEt, —$NH_2$, —NH(Me), —NH(Et), —N(Me)(Me), —$CH_2NH_2$, —$CH_2CH_2NH_2$, —$NHCO_2$t-butyl, phenyl, cyclopentyl, methyl, ethyl, isopropyl, cyclopropyl, —$NH(CH_2)_3NH_2$, —$NH(CH_2)_2NH_2$, —$NH(CH_2)_2NHEt$, —$NHCH_2$pyridyl, —$NHSO_2$phenyl, —$NHC(O)CH_2C(O)Ot$-butyl, —NHC(O)$CH_2NH_3$, —$CH_2C(CH_3)_2NH_2$, —$CH_2C(CH_3)_2NH_2$, —$NHCH_2$-imidazol-4-yl.

In certain exemplary embodiments, the Ar¹ group of formula I, and any subsets thereof, is:
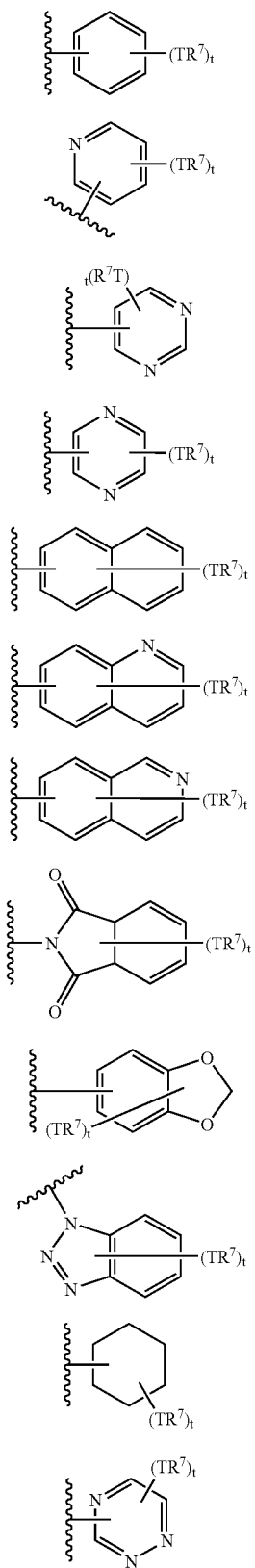
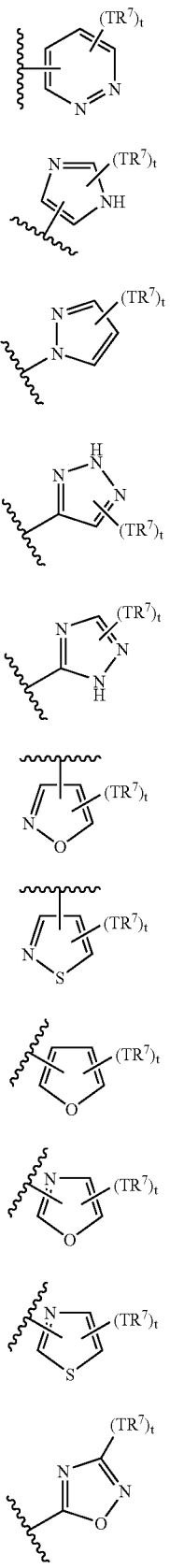

-continued

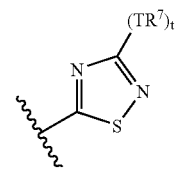

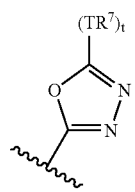

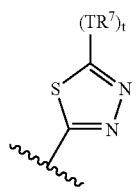

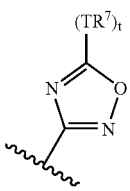

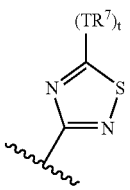

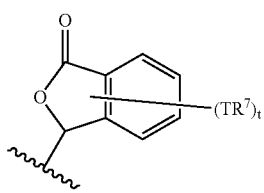

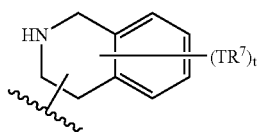

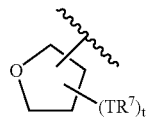

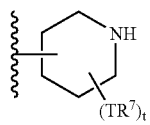

-continued

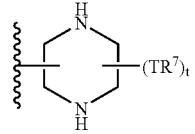 x

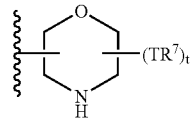 y

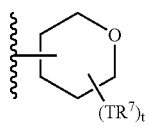 z

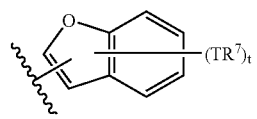 aa

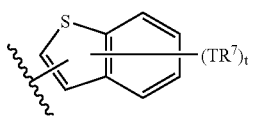 bb

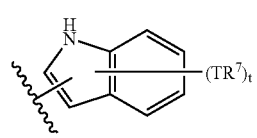 cc

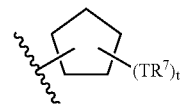 dd

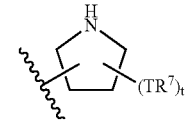 ee

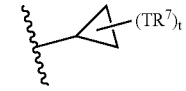 ff

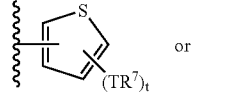 or

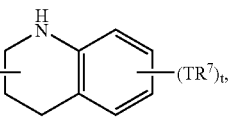

gg hh ii jj kk ll mm nn oo pp qq wherein each t is independently 0, 1, 2, 3, 4, or 5, and wherein any $Ar^1$ is bonded to $Q^2$ through any substitutable nitrogen or carbon atom, and wherein one or more hydrogen atoms on any substitutable nitrogen or carbon atom is substituted with one or more independent occurrences of $TR^7$, wherein $TR^7$ is defined generally above.

In other embodiments, the Ar¹ moiety of formula I is a, b, e, f, g, h, i, j, k, r, cc, dd, ff, jj, ll, or pp. As described generally above, each Ar¹ is optionally and independently substituted with 0-5 independent occurrences of TR⁷; wherein T is a valence bond or is a $C_1$-$C_6$ alkylidene chain wherein up to two methylene units of T are optionally replaced by —NR—, —S—, —O—, —CS—, —$CO_2$—, —OC(O)—, —C(O)—, —C(O)C(O)—, —C(O)NR—, —NRC(O)—, —$NRCO_2$—, —$SO_2$NR—, —$NRSO_2$—, —C(O)NRNR—, —NRC(O)NR—, —OC(O)NR—, —NRNR—, —$NRSO_2$NR—, —S(O)—, —$SO_2$—, —P(O)—, —$PO_2$—, or —P(O)R—; and each occurrence of R⁷ is independently R', halogen, $NO_2$, or CN.

In certain embodiments, T is a valence bond or is an optionally substituted $C_{1-6}$ alkylidene chain wherein one or two methylene units are optionally and independently replaced by —O—, —NR—, —S—, —S(O)—, —$SO_2$—, —C(O)O—, —C(O)—, —$OSO_2$—, —$NRSO_2$, —C(O)NR—, or —$SO_2$NR—, and R⁷ is R' or halogen. In other embodiments, each occurrence of TR⁷ is independently —$C_{1-3}$alkyl, —OR', —SR', —$CF_3$, —$OCF_3$, —$SCF_3$, —F, —Cl, I, —Br, —C(O)OR', —C(O)R', —O($CH_2$)$_4$N(R)(R'), —O($CH_2$)$_3$N(R)(R'), —O($CH_2$)$_2$N(R)(R'), —O($CH_2$)N(R)(R'), —O($CH_2$)$_4$C(O)N(R)(R'), —O($CH_2$)$_3$CON(R)(R'), —O($CH_2$)$_2$CON(R)(R'), —O($CH_2$)CON(R)(R'), —CON(R)(R'), —($CH_2$)$_4$OR', —($CH_2$)$_3$OR', —($CH_2$)$_2$OR', —$CH_2$OR', optionally substituted phenyl or benzyl, —N(R)(R'), —($CH_2$)$_4$N(R)(R'), —($CH_2$)$_3$N(R)(R'), —($CH_2$)$_2$N(R)(R'), —($CH_2$)N(R)(R'), $SO_2$N(R)(R'), $NRSO_2$R', —C(O)N(R)(R'), —$NRSO_2$($CH_2$)$_{1-4}$N(R)(R'), —C(O)NR($CH_2$)$_{1-4}$N(R)(R'), —C(O)O($CH_2$)$_{1-4}$N(R)(R'), or —$SO_2$R', wherein each R and R' is as defined generally above.

According to yet other embodiments, the R³ moiety of formula I is selected from any of the following:

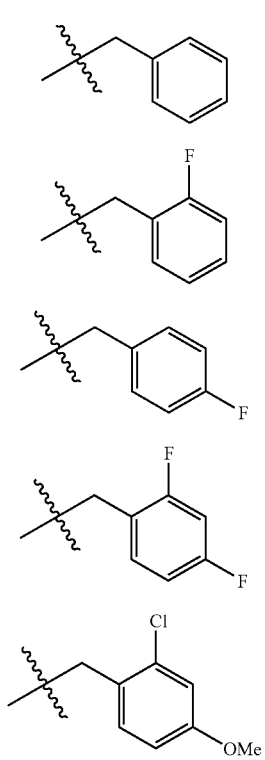

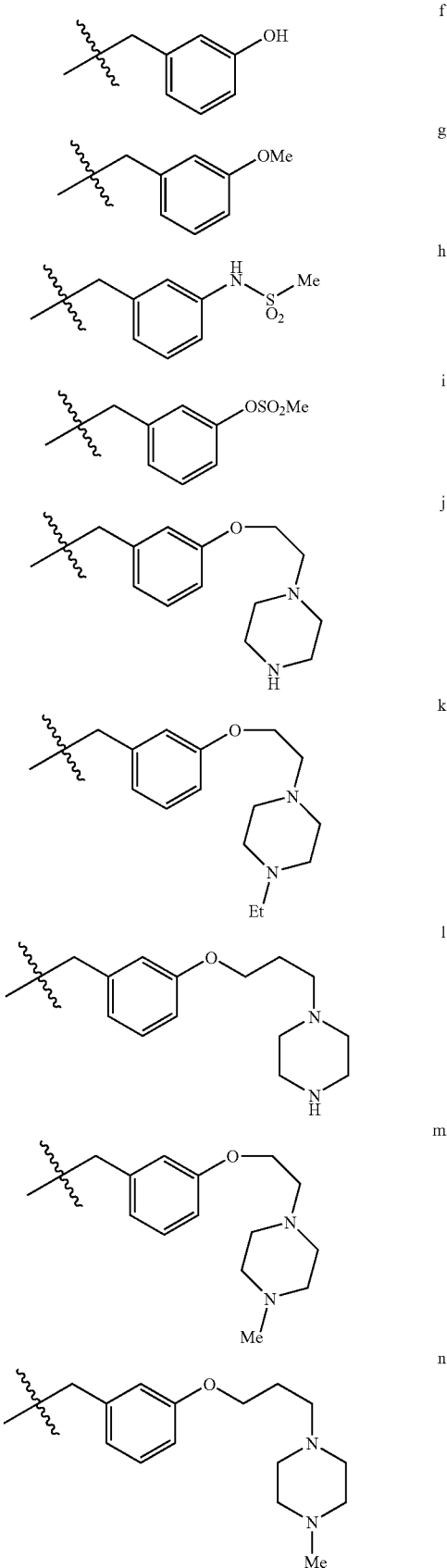

-continued

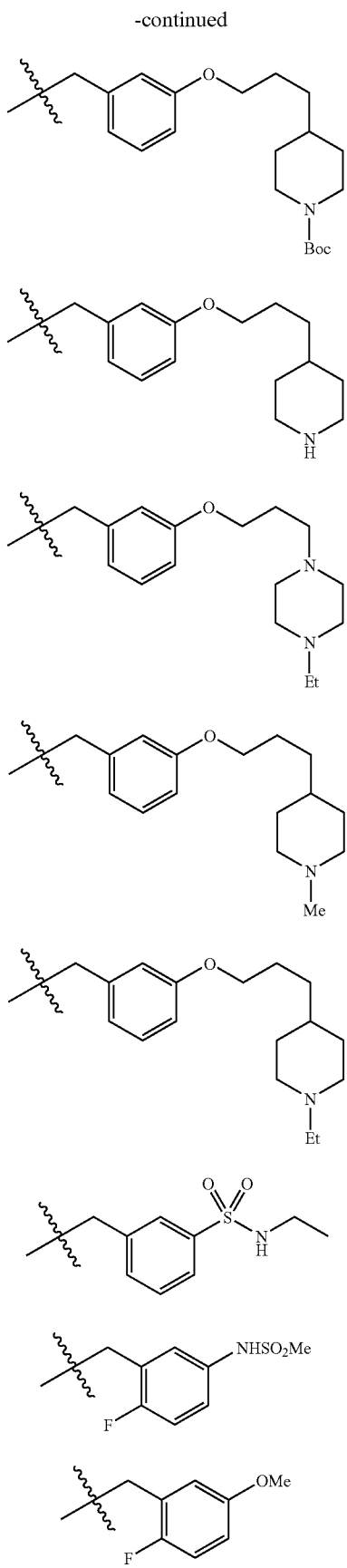

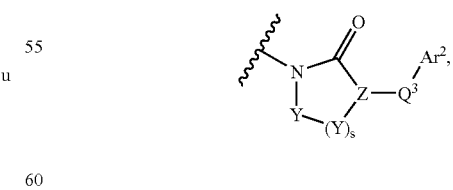

According to another embodiment, the $R^2$ and $Q^1$-$R^3$ moieties of either of formula I or II, taken together with the nitrogen atom, form the cyclic group:

where Z is CH or N, s is 1 or 2, each occurrence of Y is independently, as valency and stability permit, —C(O)—, —CS—, —SO$_2$—, —O—, —S—, —NR$^5$—, or —C(R$^5$)$_2$—, and each $R^5$ is independently $U_{(n)}R'$. Accordingly, another aspect of the present invention relates to a compound of formula IV:

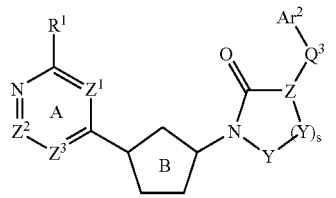

IV or a pharmaceutically acceptable salt thereof, wherein $R^1$, $Z^1$, $Z^2$, $Z^3$, Ring B, Z, Y, s, $Q^3$, and $Ar^2$ are as defined above.

In certain embodiments, the $Q^3$ moiety of either of formula I or IV is a direct bond, or is —$(CHR^6)_q$—, —$(CHR^6)_qO$—, —$(CHR^6)_qS$—, —$(CHR^6)_qS(O)_2$—, —$(CHR^6)_qS(O)$—, —$(CHR^6)_qNR$—, or —$(CHR^6)_qC(O)$—, wherein each q is independently 0, 1, 2, or 3. In certain other embodiments, each $R^6$ is independently R', —N(R)(R'), —$(CH_2)_{1-4}$N(R)(R'), —$(CH_2)_{1-4}$C(CH_3)_2$N(R)(R'), —OR', —$(CH_2)_{1-4}$OR', —NR$(CH_2)_{1-4}$N(R)(R'), —NR$(CH_2)_{1-4}$SO_2R', —NR$(CH_2)_{1-4}$COOR', or —NR$(CH_2)_{1-4}$C(O)R', or two occurrences of $R^6$, taken together with the atoms to which they are bound, form an optionally substituted 3-6-membered saturated, partially unsaturated, or fully unsaturated ring. Examples of such $R^6$ groups include, but are not limited to —$CH_2OH$, —$CH_2CH_2OH$, —OH, —OMe, —OEt, —$NH_2$, —NH(Me), —NH(Et), —N(Me)(Me), —$CH_2NH_2$, —$CH_2CH_2NH_2$, —$NHCO_2$t-butyl, phenyl, cyclopentyl, methyl, ethyl, isopropyl, cyclopropyl, —NH$(CH_2)_3NH_2$, —NH$(CH_2)_2NH_2$, —NH$(CH_2)_2NHEt$, —$NHCH_2$pyridyl, —$NHSO_2$phenyl, —$NHCOCH_2C(O)Ot$-butyl, —$NHCOCH_2NH_3$, —$CH_2C(CH_3)_2NH_2$, —$CH_2C(CH_3)_2NH_2$, —$NHCH_2$-imidazol-4-yl.

For compounds of general formula IV, exemplary $Ar^2$ groups include:

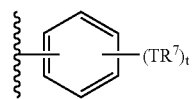
a

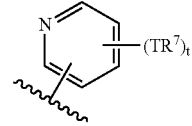
b

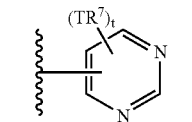
c

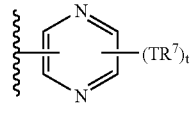
d

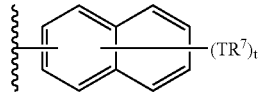
e

-continued

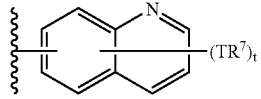
f

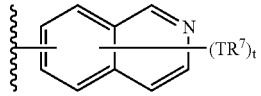
g

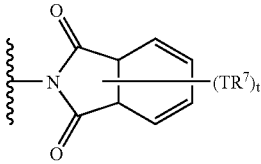
h

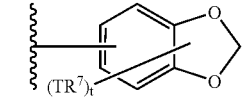
i

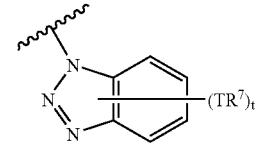
j

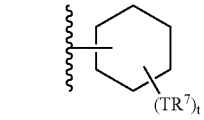
k

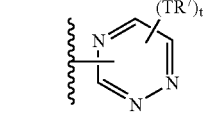
l

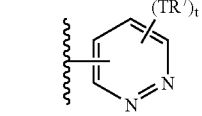
m

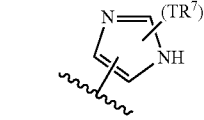
n

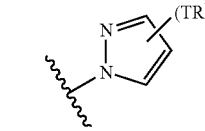
o

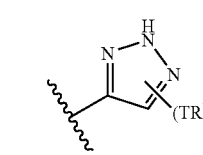
p

-continued
| | |
|---|---|
| 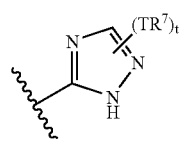 | q |
| 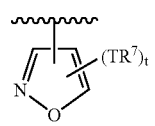 | r |
| 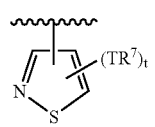 | s |
| 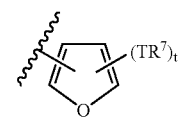 | t |
| 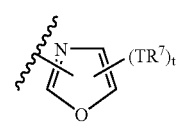 | u |
| 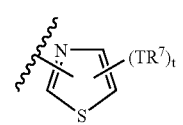 | v |
| 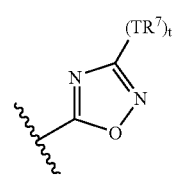 | w |
| 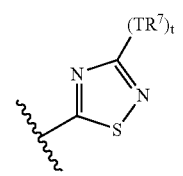 | x |
| 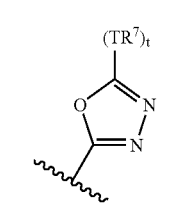 | y |
| 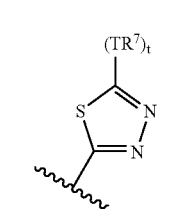 | z |
-continued
| | |
|---|---|
| 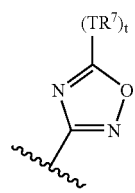 | aa |
| 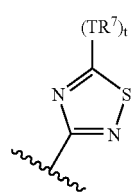 | bb |
| 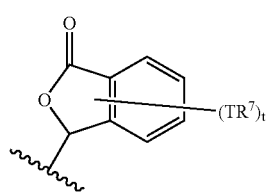 | cc |
| 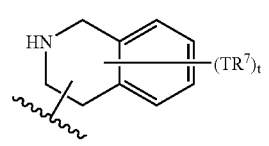 | dd |
| 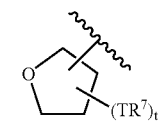 | ee |
| 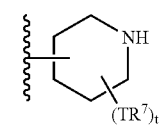 | ff |
| 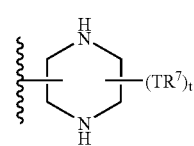 | gg |
| 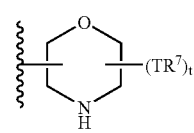 | hh |
| 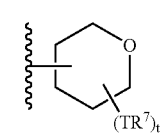 | ii |
| 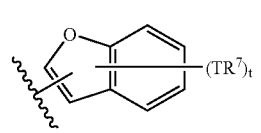 | jj |

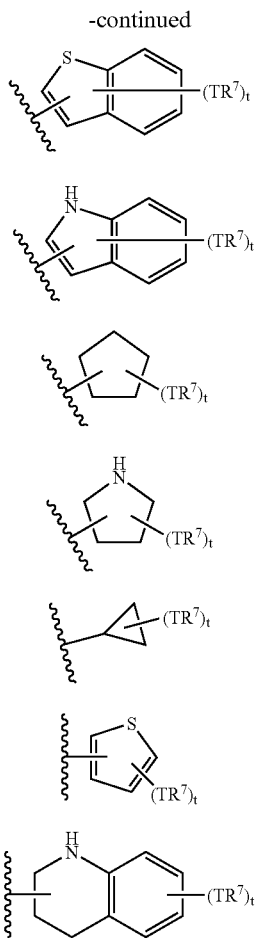

wherein each t is independently 0, 1, 2, 3, 4, or 5, and wherein any $Ar^2$ is bonded to $Q^3$ through any substitutable nitrogen or carbon atom, and wherein one or more hydrogen atoms on any substitutable nitrogen or carbon atom is substituted with one or more independent occurrences of $TR^7$, wherein $TR^7$ is defined generally above.

Other embodiments of the present invention relate to a compound of formula IV wherein $Ar^2$ is a, b, e, f, g, h, i, j, k, n, r, cc, dd, ff, jj, ll, or pp.

As described generally above, $Ar^2$ is optionally substituted with 0-5 independent occurrences of $TR^7$; wherein T is a valence bond or is a $C_1$-$C_6$ alkylidene chain wherein up to two methylene units of T are optionally replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NRCONR—, —OCONR—, —NRNR—, —NRSO$_2$NR—, —SO—, —SO$_2$—, —PO—, —PO$_2$—, or —POR—; and each occurrence of $R^7$ is independently R', halogen, NO$_2$, or CN.

In certain embodiments, T is a valence bond.

In other embodiments, T is an optionally substituted $C_{1-6}$ alkylidene chain wherein one or two methylene units are optionally and independently replaced by —O—, —NR—, —S—, —SO—, —SO$_2$—, —C(O)O—, —C(O)—, —OSO$_2$—, —NRSO$_2$, —C(O)NR—, or —SO$_2$NR—, and $R^7$ is R' or halogen. In other embodiments, each occurrence of $TR^7$ is independently —C$_{1-3}$alkyl, —OR', —SR', —CF$_3$, —OCF$_3$, —SCF$_3$, —F, —Cl, I, —Br, —C(O)OR', —C(O)R', —O(CH$_2$)$_4$N(R)(R'), —O(CH$_2$)$_3$N(R)(R'), —O(CH$_2$)$_2$N(R)(R'), —O(CH$_2$)N(R)(R'), —O(CH$_2$)$_4$C(O)N(R)(R'), —O(CH$_2$)$_3$CON(R)(R'), —O(CH$_2$)$_2$C(O)N(R)(R'), —O(CH$_2$)C(O)N(R)(R'), —C(O)N(R)(R'), —(CH$_2$)$_4$OR', —(CH$_2$)$_3$OR', —(CH$_2$)$_2$OR', —CH$_2$OR', optionally substituted phenyl or benzyl, —N(R)(R'), —(CH$_2$)$_4$N(R)(R'), —(CH$_2$)$_3$N(R)(R'), —(CH$_2$)$_2$N(R)(R'), —(CH$_2$)N(R)(R'), or —SO$_2$N(R)(R'), —NRSO$_2$R', —C(O)N(R)(R'), —NRSO$_2$(CH$_2$)$_{1-4}$N(R)(R'), —C(O)NR(CH$_2$)$_{1-4}$N(R)(R'), —C(O)O(CH$_2$)$_{1-4}$N(R)(R'), or —OSO$_2$R', wherein each R and R' is as generally above.

In certain embodiments, for compounds of either of formula I or IV, $R^5$ is hydrogen, —(CH$_2$)$_3$OR', —(CH$_2$)$_2$OR', —(CH$_2$)OR', —(CH$_2$)$_3$N(R')$_2$, —(CH$_2$)$_2$N(R')$_2$, —(CH$_2$)N(R')$_2$, or —C$_{1-4}$aliphatic.

As described generally above, Ring B is optionally substituted with zero, one or two occurrences of $R^4$, as valency permits, wherein each occurrence of $R^4$ is independently halogen, CN, NO$_2$, or U$_{(n)}$R. In some embodiments, the $R^4$ groups of any of formula I, II, III, or IV are each independently hydrogen, $C_{1-6}$aliphatic, —CN, —C(O)R, —C(O)OR, —C(O)N(R)$_2$, or halogen. In other embodiments, $R^4$ groups are each hydrogen.

In certain embodiments, for compounds of formula I, Ring A is an optionally substituted pyridyl, pyrimidinyl, 1,2,4-triazinyl, 1,3,5-triazinyl, or pyridazinyl ring. Accordingly, in certain embodiments, compounds of the present invention have one of the structures of formulae I-A, I-B, I-C, I-D, and I-E depicted below:

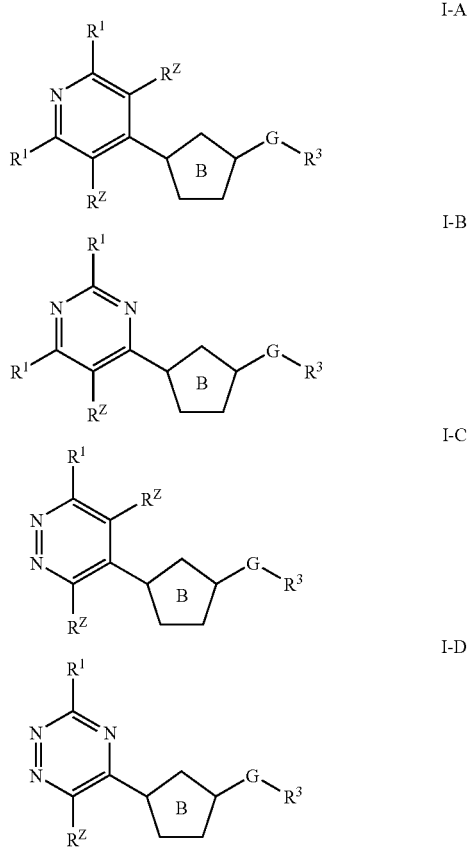

-continued

I-E

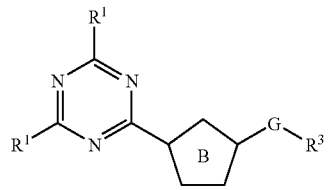

or a pharmaceutically acceptable salt thereof, wherein each $R^1$, Ring B, $R^z$, $R^3$, and G are as defined generally and in classes and subclasses above and herein.

It will also be appreciated that according to certain embodiments for compounds of formulae I-A, I-B, I-C, I-D, and I-E, $R^3$ is $Q^2$-$Ar^1$, wherein $Q^2$ and $Ar^1$ are described generally and in subsets above and herein.

According to yet other embodiments, compounds of the present invention are contemplated where any of formulae I-A, I-B, I-C, I-D, and I-E is combined with any Ring B moiety. Specifically, it will be understood that another aspect of the present invention relates to a compound of any of formulae I-A, I-B, I-C, I-D, and I-E wherein Ring B is a 5-membered heteroaryl ring selected from pyrazole, imidazole, triazole, tetrazole, furan, oxazole, isoxazole, or oxadiazole, wherein said Ring B is optionally substituted with 0-3 $R^4$ groups. According to yet another embodiment, the present invention relates to a compound of any of formulae I-A, I-B, I-C, I-D, and I-E wherein Ring B is triazole, imidazole, or oxadiazole wherein said Ring B is optionally substituted with 0-2 $R^4$ groups.

In certain embodiments, the present invention relates to a compound of any of formulae I-A, I-B, I-C, I-D, and I-E wherein Ring B is oxadiazole.

In other embodiments, the present invention relates to a compound of any of formulae I-A, I-B, I-C, I-D, and I-E wherein Ring B is imidazole optionally substituted with 0-2 $R^4$ groups.

In yet other embodiments, the present invention relates to a compound of any of formulae I-A, I-B, I-C, I-D, and I-E wherein Ring B is triazole optionally substituted with 0-1 $R^4$ group.

In certain embodiments, the present invention relates to a compound of formula I wherein G is —$NR^2$-$Q^1$-, wherein $Q^1$ is —CO—, $Q^2$ is —$CHR^6$—, q is 1 2, or 3 and said compound is of formula V:

V

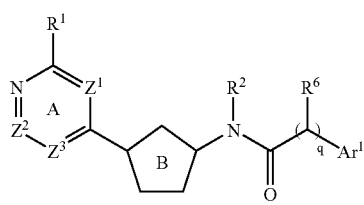

or a pharmaceutically acceptable salt thereof, wherein Ring B, $Z^1$, $Z^2$, $Z^3$, $R^1$, $R^2$, $R^6$, q, and $Ar^1$ are as defined generally and in classes and subclasses above and herein.

According to other embodiments, compounds of any of formulae I-A, I-B, I-C, I-D, and I-E are provided where G is —$NR^2$-$Q^1$-, wherein $Q^1$ is —CO—, $Q^2$ is —$CHR^6$—, q is 1 2, or 3. Accordingly, the following compounds of formulae V-A, V-B, V-C, V-D, and V-E are provided:

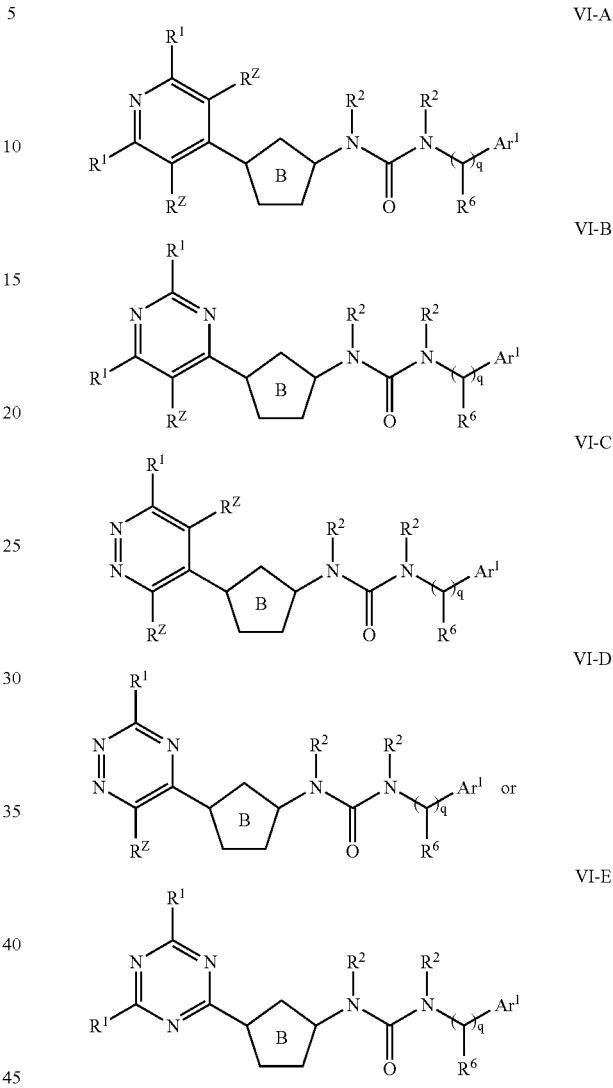

or a pharmaceutically acceptable salt thereof, wherein each $R^1$, $R^z$, Ring B, q, $R^2$, $R^6$, and $Ar^1$ are as defined generally and in classes and subclasses above and herein.

In yet other embodiments, compounds of any of formulae I-A, I-B, I-C, I-D, and I-E are provided where G is —$NR^2$-$Q^1$-, wherein $Q^1$ is —$CONR^2$—, $Q^2$ is —$CHR^6$—, q is 1 2, or 3. Accordingly, the following compounds of formulae VI-A, VI-B, VI-C, VI-D, and VI-E are provided:

VI-A

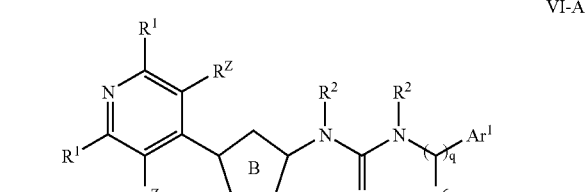

-continued

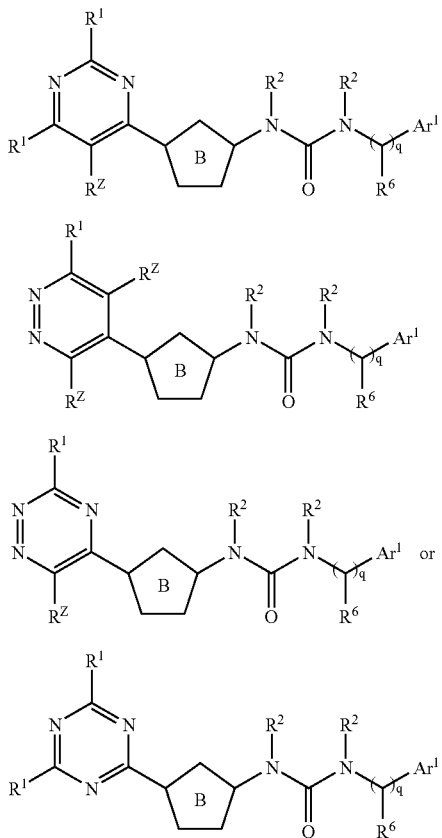

or a pharmaceutically acceptable salt thereof, wherein each $R^1$, $R^z$, Ring B, $R^2$, $R^6$, q, and $Ar^1$ are as defined generally and in classes and subclasses above and herein.

In certain embodiments, for compounds of any of formulae V-A, V-B, V-C, V-D, V-E, VI-A, VI-B, VI-C, VI-D, and VI-E compound variables are selected from one of more of the following groups:

a) each occurrence of $R^1$ is independently hydrogen, halogen, optionally substituted $C_1$-$C_4$aliphatic, OR', or SR';

b) each occurrence of $R^1$ is independently hydrogen, halogen, —$CH_3$, —$CH_2CH_3$, —OH, —$OCH_3$, or —$SCH_3$;

c) each $R^2$ is independently hydrogen, or is $U_{(n)}R'$, where n is 1, and U is —$CH_2$—, —$CH_2CH_2$—, —$CH_2CH_2CH_2$—, —$CH_2CH_2CH_2CH_2$—, —$CH_2O$—, —$CH_2S$—, —$CH_2NR$—, —$CH_2CH_2O$—, —$CH_2CH_2S$—, —$CH_2CH_2NR$—, —$CH_2CH_2CH_2O$—, —$CH_2CH_2CH_2S$—, —$CH_2CH_2CH_2NR$—, —$CH_2CH_2CH_2CH_2O$—, —$CH_2CH_2CH_2CH_2S$—, —$CH_2CH_2CH_2CH_2NR$—, —$CH_2CH_2OCH_2CH_2$—, —$(CH_2)_4NHCH_2$—, —$(CH_2)_3NHCH_2CH_2$—, or —$CH_2CH_2NHCH_2CH_2$—, wherein R' groups are hydrogen, $C_1$-$C_4$alkyl, an optionally substituted group selected from tetrahydropyranyl, pyrrolidinyl, piperidinyl, piperazinyl, morpholinyl, thiomorpholinyl, pyridinyl, imidazolyl, phenyl, or cyclohexyl, or R and R', taken together with the nitrogen atom to which they are bound, form an optionally substituted 5- or 6-membered saturated, partially unsaturated, or unsaturated heterocyclyl ring;

d) each occurrence of $R^4$ is independently hydrogen, $C_{1-6}$aliphatic, CN, C(O)R, C(O)OR, C(O)N(R)$_2$, or halogen;

e) each q is independently 1, 2, or 3;

f) each $R^6$ is independently R', —N(R)(R'), —$(CH_2)_{1-4}$N(R)(R'), —$(CH_2)_{1-4}$C(CH$_3$)$_2$N(R)(R'), —OR', —$(CH_2)_{1-4}$OR', —NR$(CH_2)_{1-4}$N(R)(R'), —NR$(CH_2)_{1-4}$SO$_2$R', —NR$(CH_2)_{1-4}$C(O)OR', or —NR$(CH_2)_{1-4}$COR', or two occurrences of $R^6$, taken together with the atoms to which they are bound, form an optionally substituted 3-6-membered saturated, partially unsaturated, or fully unsaturated ring;

g) each $R^6$ is independently $CH_2OH$, $CH_2CH_2OH$, OH, OMe, OEt, $NH_2$, NH(Me), NH(Et), N(Me)(Me), $CH_2NH_2$, $CH_2CH_2NH_2$, NHCO$_2$t-butyl, phenyl, cyclopentyl, methyl, ethyl, isopropyl, cyclopropyl, NH(CH$_2$)$_3$ NH$_2$, NH(CH$_2$)$_2$NH$_2$, NH(CH$_2$)$_2$NHEt, NHCH$_2$pyridyl, NHSO$_2$phenyl, NHCOCH$_2$COOt-butyl, NHCOCH$_2$NH$_3$, —$CH_2C(CH_3)_2NH_2$, —$CH_2C(CH_3)_2NH_2$, NHCH$_2$-imidazol-4-yl;

h) each $Ar^1$ is independently ring a, b, e, f, g, h, i, j, k, r, cc, dd, ff, jj, ll, or pp, wherein each t is independently 0, 1, 2, or 3, and each T is independently a valence bond or is an optionally substituted $C_{1-6}$ alkylidene chain wherein one or two methylene units are optionally and independently replaced by —O—, —NR—, —S—, —S(O)—, —SO$_2$—, —C(O)O—, —C(O)—, —OSO$_2$—, —NRSO$_2$, —C(O)NR—, or —SO$_2$NR—, and $R^7$ is R' or halogen; or i) each $Ar^1$ is independently ring a, b, e, f, g, h, i, j, k, r, cc, dd, ff, jj, ll, or pp, wherein each t is independently 0, 1, 2, or 3, and each occurrence of TR$^7$ is independently —$C_{1-3}$alkyl, —OR', —SR', —CF$_3$, —OCF$_3$, —SCF$_3$, —F, —Cl, I, —Br, —COOR', —COR', —O(CH$_2$)$_4$N(R)(R'), —O(CH$_2$)$_3$N(R)(R'), —O(CH$_2$)$_2$N(R)(R'), —O(CH$_2$)N(R)(R'), —O(CH$_2$)$_4$C(O)N(R)(R'), —O(CH$_2$)$_3$C(O)N(R)(R'), —O(CH$_2$)$_2$C(O)N(R)(R'), —O(CH$_2$)C(O)N(R)(R'), —C(O)N(R)(R'), —(CH$_2$)$_4$OR', —(CH$_2$)$_3$OR', —(CH$_2$)$_2$OR', —CH$_2$OR', optionally substituted phenyl or benzyl, —N(R)(R'), —(CH$_2$)$_4$N(R)(R'), —(CH$_2$)$_3$N(R)(R'), —(CH$_2$)$_2$N(R)(R'), —(CH$_2$)N(R)(R'), or SO$_2$N(R)(R'), NRSO$_2$R', C(O)N(R)(R'), —NRSO$_2$(CH$_2$)$_{1-4}$N(R)(R'), —C(O)NR(CH$_2$)$_{1-4}$N(R)(R'), —C(O)O(CH$_2$)$_{1-4}$N(R)(R'), or —OSO$_2$R'.

In other embodiments, the present invention relates to a compound of any of formulae V-A, V-B, V-C, V-D, and V-E, wherein q is 1, and $Ar^1$ is optionally substituted phenyl. Accordingly, the following compounds of formulae V-A', V-B', V-C', V-D', and V-E' are provided:

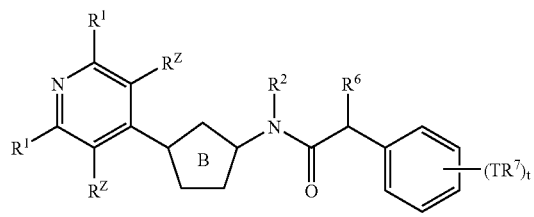

V-A'

-continued

V-B'

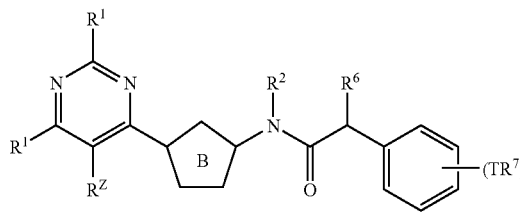

V-C'

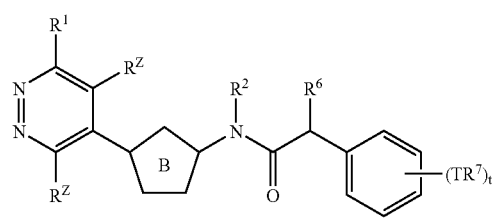

V-D'

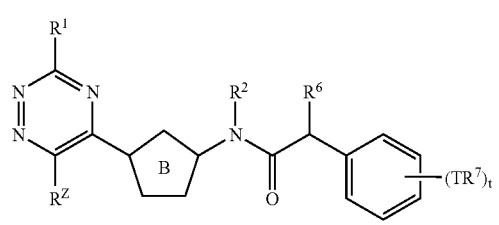

V-E'

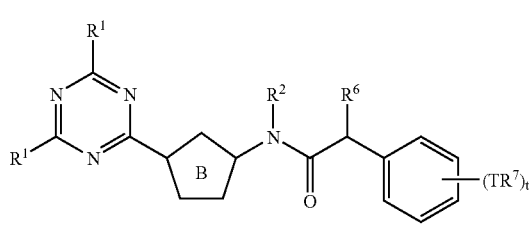

or a pharmaceutically acceptable salt thereof, wherein each $R^1$, $R^z$, Ring B, T, $R^2$, $R^6$, T and $R^7$ are as defined generally and in classes and subclasses above and herein.

In certain embodiments, the present invention relates to a compound of any of formulae V-A', V-B', V-C', V-D', and V-E', wherein:

each occurrence of $R^1$ is hydrogen;

$R^2$ is hydrogen, or is $U_{(n)}R'$, where n is 1, and U is —CH$_2$—, —CH$_2$CH$_2$—, —CH$_2$CH$_2$CH$_2$—, —CH$_2$CH$_2$CH$_2$CH$_2$—, —CH$_2$O—, —CH$_2$S—, —CH$_2$NR—, —CH$_2$CH$_2$O—, —CH$_2$CH$_2$S—, —CH$_2$CH$_2$NR—, —CH$_2$CH$_2$CH$_2$O—, —CH$_2$CH$_2$CH$_2$S—, —CH$_2$CH$_2$CH$_2$NR—, —CH$_2$CH$_2$CH$_2$CH$_2$O—, —CH$_2$CH$_2$CH$_2$CH$_2$S—, —CH$_2$CH$_2$CH$_2$CH$_2$NR—, —CH$_2$CH$_2$OCH$_2$CH$_2$—, —(CH$_2$)$_4$NHCH$_2$—, —(CH$_2$)$_3$NHCH$_2$CH$_2$—, or —CH$_2$CH$_2$NHCH$_2$CH$_2$—, wherein R' groups are hydrogen, C$_1$-C$_4$alkyl, an optionally substituted group selected from tetrahydropyranyl, pyrrolidinyl, piperidinyl, piperazinyl, morpholinyl, thiomorpholinyl, pyridinyl, imidazolyl, phenyl, or cyclohexyl, or R and R', taken together with the nitrogen atom to which they are bound, form an optionally substituted 5- or 6-membered saturated, partially unsaturated, or unsaturated heterocyclyl ring;

each occurrence of $R^4$ is independently hydrogen, C$_{1-6}$aliphatic, CN, C(O)R, C(O)OR, C(O)N(R)$_2$, or halogen;

$R^6$ is R', —N(R)(R'), —(CH$_2$)$_{1-4}$N(R)(R'), —(CH$_2$)$_{1-4}$C(CH$_3$)$_2$N(R)(R'), —OR', —(CH$_2$)$_{1-4}$OR', —NR(CH$_2$)$_{1-4}$N(R)(R'), —NR(CH$_2$)$_{1-4}$SO$_2$R', —NR(CH$_2$)$_{1-4}$COOR', or —NR(CH$_2$)$_{1-4}$COR'; and t is 0, 1, 2, or 3, and each occurrence of TR$^7$ is independently —C$_{1-3}$alkyl, —OR', —SR', —CF$_3$, —OCF$_3$, —SCF$_3$, —F, —Cl, —I, —Br, —C(O)OR', —C(O)R', —O(CH$_2$)$_4$N(R)(R'), —O(CH$_2$)$_3$N(R)(R'), —O(CH$_2$)$_2$N(R)(R'), —O(CH$_2$)N(R)(R'), —O(CH$_2$)$_4$C(O)N(R)(R'), —O(CH$_2$)$_3$C(O)N(R)(R'), —O(CH$_2$)$_2$C(O)N(R)(R'), —O(CH$_2$)C(O)N(R)(R'), —CON(R)(R'), —(CH$_2$)$_4$OR', —(CH$_2$)$_3$OR', —(CH$_2$)$_2$OR', —CH$_2$OR', optionally substituted phenyl or benzyl, —N(R)(R'), —(CH$_2$)$_4$N(R)(R'), —(CH$_2$)$_3$N(R)(R'), —(CH$_2$)$_2$N(R)(R'), —(CH$_2$)N(R)(R'), or SO$_2$N(R)(R'), NRSO$_2$R', C(O)N(R)(R'), —NRSO$_2$(CH$_2$)$_{1-4}$N(R)(R'), —C(O)NR(CH$_2$)$_{1-4}$N(R)(R'), —C(O)O(CH$_2$)$_{1-4}$N(R)(R'), or —OSO$_2$R'.

In other exemplary embodiments, for compounds of formulae I-A, I-B, I-C, I-D, and I-E, for each of the above-described classes and subclasses of compounds wherein G is —NR$^2$-Q$^1$-, R$^2$ and Q$^1$-R$^3$, taken together with the nitrogen atom, form the cyclic group:

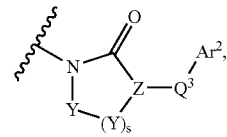

where Z is CH or N, s is 1 or 2, each occurrence of Y is independently, as valency and stability permit, —CO—, —CS—, —SO$_2$—, —O—, —S—, —NR$^5$—, or —C(R$^5$)$_2$—, and R$^5$ is U$_n$R', wherein Q$^3$, Ar$^2$, and R$^5$ are described generally above and in classes and subclasses above and herein.

According to yet another embodiment, the following compounds of formulae VII-A, VII-B, VII-C, VII-D, and VII-E are provided:

VII-A

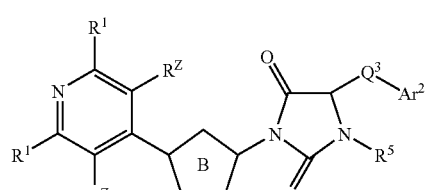

VII-B

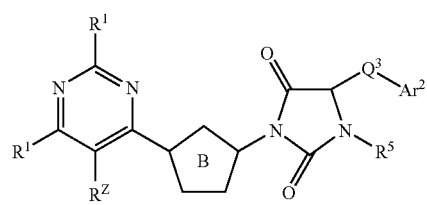

VII-C

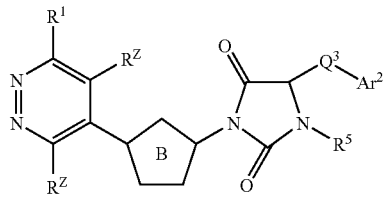

VII-D

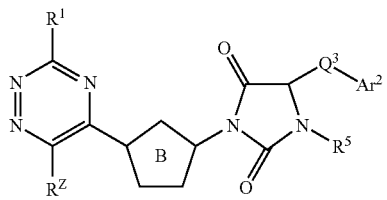

VII-E

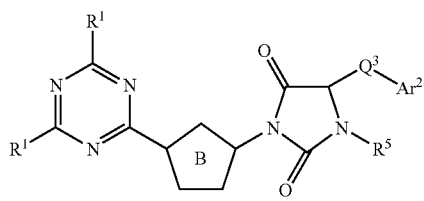

or a pharmaceutically acceptable salt thereof, wherein each $R^1$, $R^z$, Ring B, $R^5$, $Q^3$, and $Ar^2$ are as defined generally and in classes and subclasses above and herein.

According to another embodiment, the following compounds of formulae VII-A', VII-B', VII-C', VII-D', and VII-E' are provided:

VII-A'

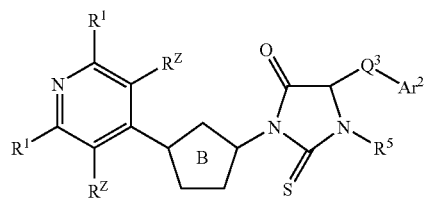

VII-B'

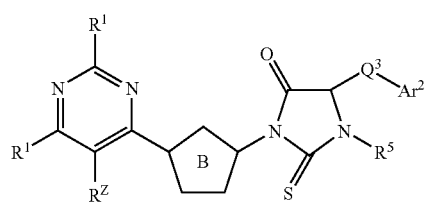

VII-C'

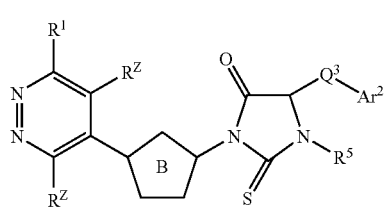

VII-D'

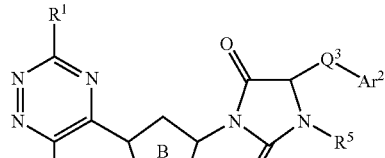

VII-E'

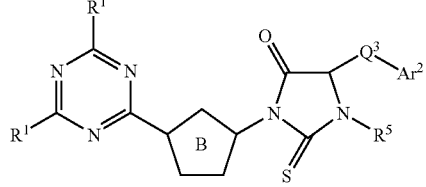

or a pharmaceutically acceptable salt thereof, wherein each $R^1$, $R^z$, Ring B, $R^5$, $Q^3$, and $Ar^2$ are as defined generally and in classes and subclasses above and herein.

In other exemplary embodiments, for compounds of formulae I-A, I-B, I-C, I-D, and I-E, for each of the above-described classes and subclasses of compounds, $R^2$ and $Q^1$-$R^3$, taken together with the nitrogen atom, form a cyclic group:

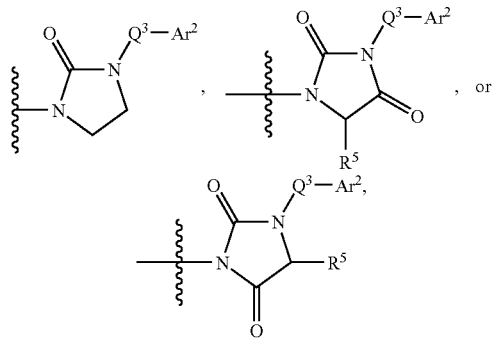

wherein each $Q^3$, $R^5$, and $Ar^2$ are described generally above and in classes and subclasses above and herein.

In still other exemplary embodiments, for compounds of formulae I-A, I-B, I-C, I-D, and I-E, for each of the above-described classes and subclasses of compounds, where G is —$NR^2$-$Q^1$-, and $R^2$ and $Q^1$-$R^3$, taken together with the atoms to which they are bound form a 6-membered cyclic group:

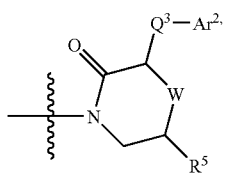

wherein $Q^3$ and $Ar^2$ are described generally above and in classes and subclasses above and herein and wherein W is O, $NR^5$, or $CHR^5$.

In certain embodiments, for compounds of formulae I-A, I-B, I-C, I-D, and I-E wherein G is —$NR^2$-$Q^1$-, and $R^2$ and $Q^1$-$R^3$, taken together with the atoms to which they are bound form a ring as described above, compound variables are selected from one of more of the following groups:

a) each occurrence of $R^1$ is hydrogen, halogen, optionally substituted $C_1$-$C_4$aliphatic, OR', or SR';
b) each occurrence of $R^4$ is independently hydrogen, $C_{1-6}$aliphatic, CN, C(O)R, C(O)OR, C(O)N(R)$_2$, or halogen;
c) $R^5$ is hydrogen, (CH$_2$)$_3$OR', (CH$_2$)$_2$OR', (CH$_2$)OR', (CH$_2$)$_3$N(R')$_2$, (CH$_2$)$_2$N(R')$_2$, (CH$_2$)N(R')$_2$, or $C_{1-4}$aliphatic;
d) $Q^3$ is a direct bond, or is —(CHR$^6$)$_q$—, —(CHR$^6$)$_q$O—, —(CHR$^6$)$_q$S—, —(CHR$^6$)$_q$S(O)$_2$—, —(CHR$^6$)$_q$S(O)—, —(CHR$^6$)$_q$NR—, or —CHR$^6$)$_q$C(O)—, wherein q is 0, 1, 2, or 3; and
e) Ar$^2$ is ring a, b, e, f, g, h, i, j, k, n, r, cc, dd, ff, jj, ll, or pp, wherein t is 0, 1, 2, or 3, and T is a valence bond or is an optionally substituted $C_1$-$C_6$ alkylidene chain wherein one or two methylene units are optionally and independently replaced by —O—, —NR—, —S—, —SO$_2$—, —C(O)O—, —C(O)—, —OSO$_2$—, —NRSO$_2$, —C(O)NR—, or —SO$_2$NR—, and $R^7$ is R' or halogen.

In certain other embodiments, for compounds of formulae I-A, I-B, I-C, I-D, and I-E wherein G is —NR$^2$-Q$^1$-, and $R^2$ and $Q^1$-$R^3$, taken together with the atoms to which they are bound form a ring as described above, compound variables are selected from one of more of the following groups:

a) each occurrence of $R^1$ is independently hydrogen, halogen, —CH$_3$, —CH$_2$CH$_3$, —OH, —OCH$_3$, or —SCH$_3$;
b) each occurrence of $R^4$ is independently hydrogen, $C_{1-6}$aliphatic, CN, C(O)R, C(O)OR, CON(R)$_2$, or halogen;
c) $R^5$ is hydrogen, (CH$_2$)$_3$OR', (CH$_2$)$_2$OR', (CH$_2$)OR', (CH$_2$)$_3$N(R')$_2$, (CH$_2$)$_2$N(R')$_2$, (CH$_2$)N(R')$_2$, or $C_{1-4}$aliphatic;
d) $Q^3$ is a direct bond, or is —(CHR$^6$)$_q$—, —(CHR$^6$)$_q$O—, —(CHR$^6$)$_q$S—, —(CHR$^6$)$_q$S(O)$_2$—, —(CHR$^6$)$_q$S(O)—, —(CHR$^6$)$_q$NR—, or —(CHR$^6$)$_q$C(O)—, wherein q is 0, 1, 2, or 3; and
e) Ar$^2$ is ring a, b, e, f, g, h, i, j, k, n, r, cc, dd, ff, jj, ll, or pp, wherein t is 0, 1, 2, or 3, and each occurrence of TR$^7$ is independently —$C_{1-3}$alkyl, —OR', —SR', —CF$_3$, —OCF$_3$, —SCF$_3$, —F, —Cl, I, —Br, —COOR', —COR', —O(CH$_2$)$_4$N(R)(R'), —O(CH$_2$)$_3$N(R)(R'), —O(CH$_2$)$_2$N(R)(R'), —O(CH$_2$)N(R)(R'), —O(CH$_2$)$_4$CON(R)(R'), —O(CH$_2$)$_3$CON(R)(R'), —O(CH$_2$)$_2$CON(R)(R'), —O(CH$_2$)CON(R)(R'), —CON(R)(R'), —(CH$_2$)$_4$OR', —(CH$_2$)$_3$OR', —(CH$_2$)$_2$OR', —CH$_2$OR', optionally substituted phenyl or benzyl, —N(R)(R'), —(CH$_2$)$_4$N(R)(R'), —(CH$_2$)$_3$N(R)(R'), —(CH$_2$)$_2$N(R)(R'), —(CH$_2$)N(R)(R'), SO$_2$N(R)(R'), NRSO$_2$R', CON(R)(R'), —NRSO$_2$(CH$_2$)$_{1-4}$N(R)(R'), —CONR(CH$_2$)$_{1-4}$N(R)(R'), —COO(CH$_2$)$_{1-4}$N(R)(R'), or —OSO$_2$R'.

In other embodiments, for compounds of formulae I-A, I-B, I-C, I-D, and I-E wherein G is —NR$^2$-Q$^1$-, and $R^2$ and $Q^1$-$R^3$, taken together with the atoms to which they are bound form a ring as described above, Ar$^2$ is optionally substituted phenyl.

In still other embodiments, for compounds of formulae I-A, I-B, I-C, I-D, and I-E wherein G is —NR$^2$-Q$^1$-, and $R^2$ and $Q^1$-$R^3$, taken together with the atoms to which they are bound form a ring as described above:

Ar$^2$ is optionally substituted phenyl;
each occurrence of $R^1$ is hydrogen;
each occurrence of $R^4$ is independently hydrogen, $C_{1-6}$aliphatic, CN, C(O)R, C(O)OR, C(O)N(R)$_2$, or halogen;

$R^5$ is hydrogen, (CH$_2$)$_3$OR', (CH$_2$)$_2$OR', (CH$_2$)OR', (CH$_2$)$_3$ N(R')$_2$, (CH$_2$)$_2$N(R')$_2$, (CH$_2$)N(R')$_2$, or $C_{1-4}$aliphatic;

$Q^3$ is a direct bond, or is —(CHR$^6$)$_q$—, —(CHR$^6$)$_q$O—, —(CHR$^6$)$_q$S—, —(CHR$^6$)$_q$S(O)$_2$—, —(CHR$^6$)$_q$S(O)—, —(CHR$^6$)$_q$NR—, or —CHR$^6$)$_q$C(O)—, wherein q is 0, 1, 2, or 3; and t is 0, 1, 2, or 3, and each occurrence of TR$^7$ is independently —$C_{1-3}$alkyl, —OR', —SR', —CF$_3$, —OCF$_3$, —SCF$_3$, —F, —Cl, I, —Br, —C(O)OR', —C(O)R', —O(CH$_2$)$_4$N(R)(R'), —O(CH$_2$)$_3$N(R)(R'), —O(CH$_2$)$_2$N(R)(R'), —O(CH$_2$)N(R)(R'), —O(CH$_2$)$_4$C(O)N(R)(R'), —O(CH$_2$)$_3$C(O)N(R)(R'), —O(CH$_2$)$_2$C(O)N(R)(R'), —O(CH$_2$)C(O)N(R)(R'), —C(O)N(R)(R'), —(CH$_2$)$_4$OR', —(CH$_2$)$_3$OR', —(CH$_2$)$_2$OR', —CH$_2$OR', optionally substituted phenyl or benzyl, —N(R)(R'), —(CH$_2$)$_4$N(R)(R'), —(CH$_2$)$_3$N(R)(R'), —(CH$_2$)$_2$N(R)(R'), —(CH$_2$)N(R)(R'), or SO$_2$N(R)(R'), NRSO$_2$R', C(O)N(R)(R'), —NRSO$_2$(CH$_2$)$_{1-4}$N(R)(R'), —C(O)NR(CH$_2$)$_{1-4}$N(R)(R'), —C(O)O(CH$_2$)$_{1-4}$N(R)(R'), or —OSO$_2$R'.

Representative examples of compounds of formula I are set forth below in Table 1 below.

TABLE 1

Compounds of Formula I

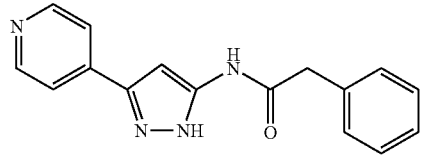

I-1

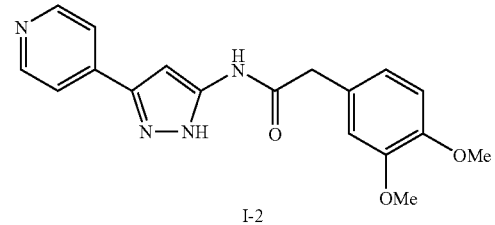

I-2

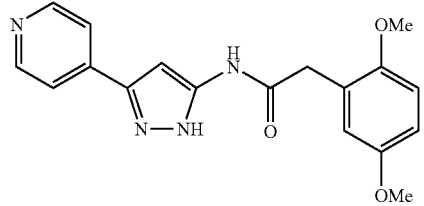

I-3

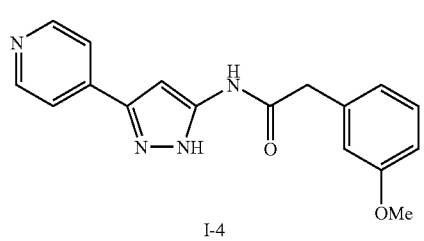

I-4

TABLE 1-continued

Compounds of Formula I

I-5

I-6

I-7

I-8

I-9

I-10

I-11

I-12

TABLE 1-continued

Compounds of Formula I

I-13

I-14

I-15

I-16

I-17

I-18

TABLE 1-continued
Compounds of Formula I
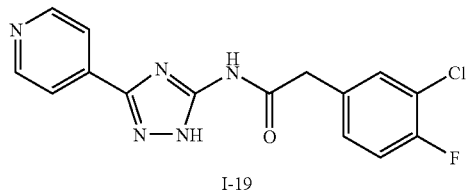
I-19
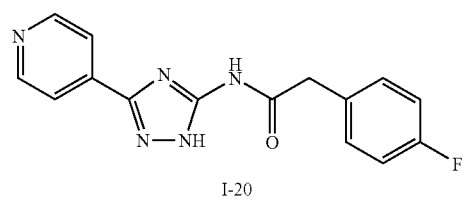
I-20
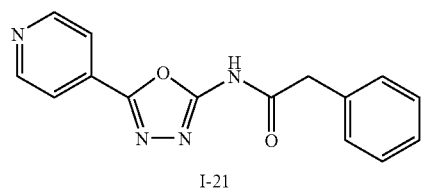
I-21
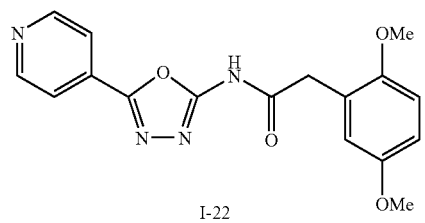
I-22
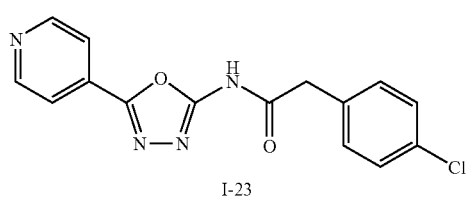
I-23
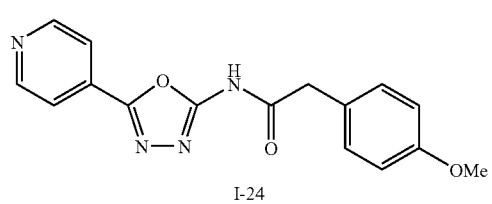
I-24
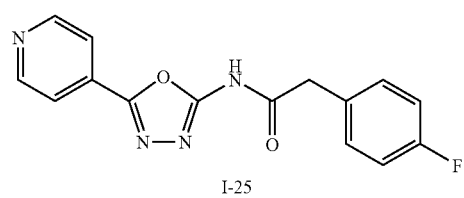
I-25
TABLE 1-continued
Compounds of Formula I
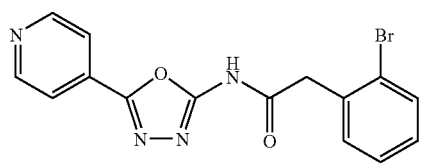
I-26
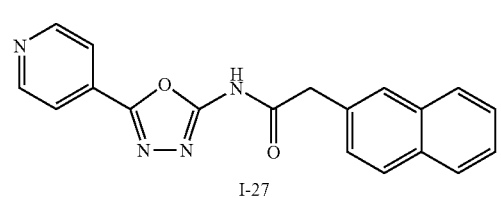
I-27
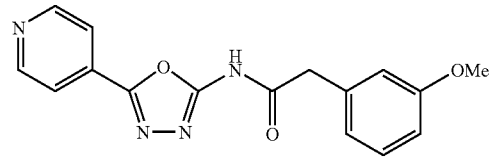
I-28
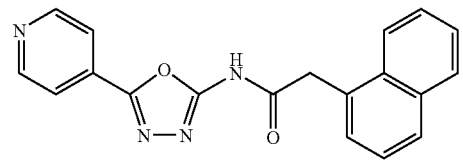
I-29
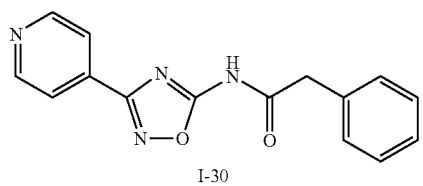
I-30
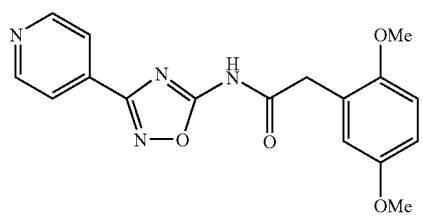
I-31
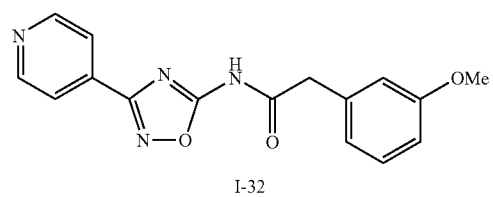
I-32

TABLE 1-continued

Compounds of Formula I

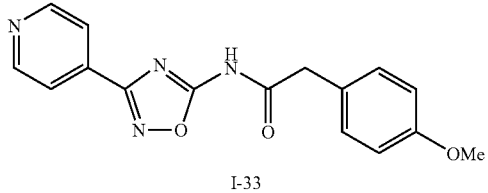

I-33

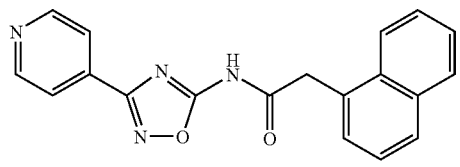

I-34

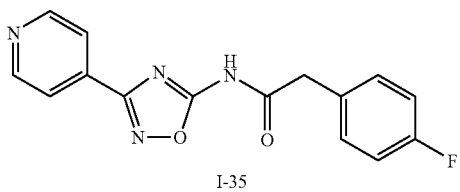

I-35

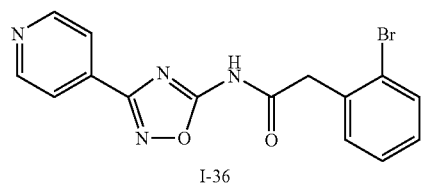

I-36

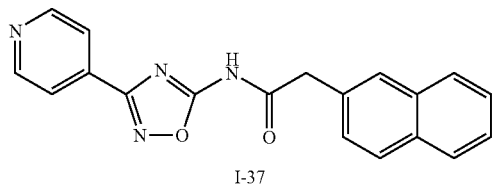

I-37

4. Uses, Formulation and Administration

Pharmaceutically Acceptable Compositions

As discussed above, the present invention provides compounds that are inhibitors of protein kinases, and thus the present compounds are useful for the treatment of diseases, disorders, and conditions including, but not limited to a proliferative disorder, a cardiac disorder, a neurodegenerative disorder, psychotic disorders, an autoimmune disorder, a condition associated with organ transplant, an inflammatory disorder, an immunologically mediated disorder, a viral disease, or a bone disorder. In preferred embodiments, the compounds are useful for the treatment of allergy, asthma, diabetes, Alzheimer's disease, Huntington's disease, Parkinson's disease, AIDS-associated dementia, amyotrophic lateral sclerosis (AML, Lou Gehrig's disease), multiple sclerosis (MS), schizophrenia, cardiomyocyte hypertrophy, reperfusion/ischemia (e.g., stroke), baldness, cancer, hepatomegaly, cardiovascular disease including cardiomegaly, cystic fibrosis, viral disease, autoimmune diseases, atherosclerosis, restenosis, psoriasis, inflammation, hypertension, angina pectoris, cerebrovascular contraction, peripheral circulation disorder, premature birth, arteriosclerosis, vasospasm (cerebral vasospasm, coronary vasospasm), retinopathy, erectile dysfunction (ED), AIDS, osteoporosis, Crohn's Disease and colitis, neurite outgrowth, and Raynaud's Disease. In preferred embodiments, the disease, condition, or disorder is atherosclerosis, hypertension, erectile dysfunction (ED), reperfusion/ischemia (e.g., stroke), or vasospasm (cerebral vasospasm and coronary vasospasm).

Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a ROCK, ERK, or GSK kinase, or members of the AGC sub-family of protein kinases (e.g., PKA, PDK, $p70^{S6K}$-1 and -2, and AKT).

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts.

This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Uses of Compounds and Pharmaceutically Acceptable Compositions

In yet another aspect, a method for the treatment or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder is provided comprising administering an effective amount of a compound, or a pharmaceutically acceptable composition comprising a compound to a subject in need thereof. In certain embodiments of the present invention an "effective amount" of the compound or pharmaceutically acceptable composition is that amount effective for treating or lessening the severity of a proliferative disorder, a cardiac disorder, a neurodegenerative disorder, a psychotic disorder, an autoimmune disorder, a condition associated with organ transplant, an inflammatory disorder, an immunologically mediated disorder, a viral disease, or a bone disorder. The compounds and compositions, according to the method of the present invention, may be administered using any amount and any route of administration effective for treating or lessening the severity of a proliferative disorder, a cardiac disorder, a neurodegenerative disorder, an autoimmune disorder, a condition associated with organ transplant, an inflammatory disorder, an immunologically mediated disorder, a viral disease, or a bone disorder. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of protein kinases. In one embodiment, the compounds and compositions of the invention are inhibitors of one or more of ROCK, ERK, or GSK kinase, or members of the AGC sub-family of protein kinases (e.g., PKA, PDK, $p70^{S6K}$-1 and -2, and AKT), and thus, without wishing to be bound by any particular theory, the compounds and compositions are particularly useful for treating or lessening the severity of a disease, condition, or disorder where activation of one or more of ROCK, ERK, or GSK kinase, or members of the AGC sub-family of protein kinases (e.g., PKA, PDK, $p70^{S6K}$-1 and -2, and AKT) is implicated in the disease, condition, or disorder. When activation of ROCK, ERK, or GSK kinase, or members of the AGC sub-family of protein kinases (e.g., PKA, PDK, p70$^{S6K}$-1 and -2, and AKT) is implicated in a particular disease, condition, or disorder, the disease, condition, or disorder may also be referred to as a "ROCK-, ERK-, GSK-, or AGC- (e.g., PKA, PDK, p70$^{S6K}$-1 and -2, and AKT) mediated disease" or disease symptom. Accordingly, in another aspect, the present invention provides a method for treating or lessening the severity of a disease, condition, or disorder where activation or one or more of ROCK, ERK, or GSK kinase, or members of the AGC sub-family of protein kinases (e.g., PKA, PDK, p70$^{S6K}$-1 and -2, and AKT) is implicated in the disease state.

The activity of a compound utilized in this invention as an inhibitor of ROCK, ERK, or GSK kinase, or members of the AGC sub-family of protein kinases (e.g., PKA, PDK, p70$^{S6K}$-1 and -2, and AKT), may be assayed in vitro, in vivo or in a cell line. In vitro assays include assays that determine inhibition of either the phosphorylation activity or ATPase activity of activated ROCK, ERK, or GSK kinase, or members of the AGC sub-family of protein kinases (e.g., PKA, PDK, p70$^{S6K}$-1 and -2, and AKT). Alternate in vitro assays quantitate the ability of the inhibitor to bind to ROCK, ERK, or GSK kinase, or members of the AGC sub-family of protein kinases (e.g., PKA, PDK, p70$^{S6K}$-1 and -2, and AKT). Inhibitor binding may be measured by radiolabelling the inhibitor prior to binding, isolating the inhibitor/ROCK, inhibitor/ERK, inhibitor/GSK kinase, or inhibitor/AGC (e.g., PKA, PDK, p70$^{S6K}$-1 and -2, and AKT) complex and determining the amount of radiolabel bound. Alternatively, inhibitor binding may be determined by running a competition experiment where new inhibitors are incubated with ROCK, ERK, or GSK kinase, or members of the AGC sub-family of protein kinases (e.g., PKA, PDK, p70$^{S6K}$-1 and -2, and AKT) bound to known radioligands.

The term "measurably inhibit", as used herein means a measurable change in ROCK, ERK, or GSK kinase, or members of the AGC sub-family of protein kinases (e.g., PKA, PDK, p70$^{S6K}$-1 and -2, and AKT) activity between a sample comprising said composition and a ROCK, ERK, or GSK kinase, or members of the AGC sub-family of protein kinases (e.g., PKA, PDK, p70$^{S6K}$-1 and -2, and AKT) kinase and an equivalent sample comprising ROCK, ERK, or GSK kinase, or members of the AGC sub-family of protein kinases (e.g., PKA, PDK, p70$^{S6K}$-1 and -2, and AKT) kinase in the absence of said composition.

The terms "AKT-mediated disease" or "AKT-mediated condition", as used herein, mean any disease or other deleterious condition in which AKT is known to play a role. The terms "AKT-mediated disease" or "AKT-mediated condition" also mean those diseases or conditions that are alleviated by treatment with a AKT inhibitor. AKT-mediated diseases or conditions include, but are not limited to, proliferative disorders, cancer, and neurodegenerative disorders. The association of AKT, also known as protein kinase B, with various diseases has been described [Khwaja, A. *Nature* 1999, 401, 33-34; Yuan, Z. Q. et al., *Oncogene* 2000, 19, 2324-2330; Namikawa, K. et al., *The Journal of Neuroscience* 2000, 20, 2875-2886].

Accordingly, another embodiment of the present invention relates to treating or lessening the severity of one or more diseases in which AKT is known to play a role. Specifically, the present invention relates to a method of treating or lessening the severity of a disease or condition selected from proliferative disorders, cancer, and neurodegenerative disorders, wherein said method comprises administering to a patient in need thereof a composition according to the present invention.

The term "PDK1-mediated condition" or "disease", as used herein, means any disease or other deleterious condition in which PDK1 is known to play a role. The term "PDK1-mediated condition" or "disease" also means those diseases or conditions that are alleviated by treatment with a PDK1 inhibitor. PDK1-mediated diseases or conditions include, but are not limited to, proliferative disorders, and cancer. Preferably, said cancer is selected from pancreatic, prostate, or ovarian cancer.

Accordingly, another embodiment of the present invention relates to treating or lessening the severity of one or more diseases in which PDK1 is known to play a role. Specifically, the present invention relates to a method of treating or lessening the severity of a cancer selected from pancreatic, prostate, or ovarian, wherein said method comprises administering to a patient in need thereof a composition according to the present invention.

The term "PKA-mediated condition" or "disease", as used herein, means any disease or other deleterious condition in which PKA is known to play a role. The term "PKA-mediated condition" or "disease" also means those diseases or conditions that are alleviated by treatment with a PKA inhibitor. PKA-mediated diseases or conditions include, but are not limited to, proliferative disorders and cancer.

Accordingly, another embodiment of the present invention relates to treating or lessening the severity of one or more diseases in which PKA is known to play a role. Specifically, the present invention relates to a method of treating or lessening the severity of a cancer, wherein said method comprises administering to a patient in need thereof a composition according to the present invention.

The term "p70$^{S6K}$-mediated condition" or "disease", as used herein, means any disease or other deleterious condition in which p70$^{S6K}$ is known to play a role. The term "p70$^{S6K}$-mediated condition" or "disease" also means those diseases or conditions that are alleviated by treatment with a p70$^{S6K}$ inhibitor. p70$^{S6K}$-mediated diseases or conditions include, but are not limited to, proliferative disorders, such as cancer and tuberous sclerosis.

Accordingly, another embodiment of the present invention relates to treating or lessening the severity of one or more diseases in which p70$^{S6K}$ is known to play a role. Specifically, the present invention relates to a method of treating or lessening the severity of a disease or condition selected from proliferative disorders, such as cancer and tuberous sclerosis, wherein said method comprises administering to a patient in need thereof a composition according to the present invention.

The term "ERK-mediated condition" or "disease", as used herein, means any disease or other deleterious condition in which ERK is known to play a role. The term "ERK-mediated condition" or "disease" also means those diseases or conditions that are alleviated by treatment with an ERK inhibitor. Such conditions include, without limitation, cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders, and hormone-related diseases. The term "cancer" includes, but is not limited to the following cancers: breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Accordingly, another embodiment of the present invention relates to treating or lessening the severity of one or more diseases in which ERK is known to play a role. Specifically, the present invention relates to a method of treating or lessening the severity of a disease or condition selected from cancer, stroke, diabetes, hepatomegaly, cardiovascular disease including cardiomegaly, Alzheimer's disease, cystic fibrosis, viral disease, autoimmune diseases, atherosclerosis, restenosis, psoriasis, allergic disorders including asthma, inflammation, neurological disorders and hormone-related diseases, wherein said method comprises administering to a patient in need thereof a composition according to the present invention.

According to another embodiment, the present invention relates to a method of treating a cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia.

Another embodiment relates to a method of treating melanoma, breast cancer, colon cancer, or pancreatic cancer in a patient in need thereof.

ERK-2 protein kinase and its implication in various diseases has been described [Bokemeyer et al., *Kidney Int.* 1996, 49, 1187; Anderson et al., *Nature* 1990, 343, 651; Crews et al., *Science* 1992, 258, 478; Bjorbaek et al., *J. Biol. Chem.* 1995, 270, 18848; Rouse et al., *Cell* 1994, 78, 1027; Raingeaud et al., *Mol. Cell Biol.* 1996, 16, 1247; Chen et al., *Proc. Natl. Acad. Sci. USA* 1993, 90, 10952; Oliver et al., *Proc. Soc. Exp. Biol. Med.* 1995, 210, 162; Moodie et al., *Science* 1993, 260, 1658; Frey and Mulder, *Cancer Res.* 1997, 57, 628; Sivaraman et al., *J Clin. Invest.* 1997, 99, 1478; Whelchel et al., *Am. J. Respir. Cell Mol. Biol.* 1997, 16, 589].

The term "GSK3-mediated disease" or "condition", as used herein means any disease or other deleterious condition in which GSK3 is known to play a role. Accordingly, another embodiment of the present invention relates to treating or lessening the severity of one or more diseases in which GSK3 is known to play a role. Specifically, the present invention relates to a method of treating or lessening the severity of a disease or condition selected from autoimmune disease, an inflammatory disease, a metabolic disorder, a psychiatric disorder, diabetes, an angiogenic disorder, tauopothy, a neurological or neurodegenerative disorder, a spinal cord injury, glaucoma, baldness, or a cardiovascular disease wherein said method comprises administering to a patient in need thereof a composition according to the present invention.

According to another embodiment, the present invention relates to a method for treating or lessening the severity of a disease or condition selected from allergy, asthma, diabetes, Alzheimer's disease, Huntington's disease, Parkinson's disease, AIDS-associated dementia, amyotrophic lateral sclerosis (ALS, Lou Gehrig's disease), multiple sclerosis (MS), an injury due to head trauma, schizophrenia, anxiety, bipolar disorder, tauopothy, a spinal cord or peripheral nerve injury, myocardial infarction, cardiomyocyte hypertrophy, glaucoma, attention deficit disorder (ADD), depression, a sleep disorder, reperfusion/ischemia, stroke, an angiogenic disorder, or baldness, wherein said method comprises administering to a patient in need thereof a compound of the present invention or composition thereof.

According to one embodiment, the method of the present invention relates to treating or lessening the severity of stroke, wherein said method comprises administering to a patient in need thereof a compound of the present invention or composition thereof.

According to another embodiment, the method of the present invention relates to treating or lessening the severity of a neurodegenerative or neurological disorder, wherein said method comprises administering to a patient in need thereof a compound of the present invention or composition thereof.

Yet another embodiment of the present invention relates to a method of treating depression, wherein said method comprises administering to a patient in need thereof a compound of the present invention or composition thereof.

Another aspect of the present invention relates to a method of decreasing sperm motility in a male patient comprising administering to said patient a compound of the present invention or composition thereof.

The term "ROCK-mediated condition" or "disease", as used herein, means any disease or other deleterious condition in which ROCK is known to play a role. The term "ROCK-mediated condition" or "disease" also means those diseases or conditions that are alleviated by treatment with a ROCK inhibitor. Such conditions include, without limitation, hypertension, angina pectoris, cerebrovascular contraction, asthma, peripheral circulation disorder, premature birth, cancer, erectile dysfunction, arteriosclerosis, spasm (cerebral vasospasm and coronary vasospasm), retinopathy (e.g., glaucoma), inflammatory disorders, autoimmune disorders, AIDS, osteoporosis, myocardial hypertrophy, ischemia/reperfusion-induced injury, and endothelial dysfunction.

In other embodiments, the invention relates to a method of enhancing glycogen synthesis and/or lowering blood levels of glucose in a patient in need thereof, comprising administering to said patient a therapeutically effective amount of a composition comprising a compound of formula I. This method is especially useful for diabetic patients.

In yet another embodiment, the invention relates to a method of inhibiting the production of hyperphosphorylated Tau protein in a patient in need thereof, comprising administering to said patient a therapeutically effective amount of a composition comprising a compound of formula I. This method is especially useful in halting or slowing the progression of Alzheimer's disease.

In still another embodiments, the invention relates to a method of inhibiting the phosphorylation of β-catenin in a patient in need thereof, comprising administering to said patient a therapeutically effective amount of a composition comprising a compound of formula I. This method is especially useful for treating schizophrenia.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated".

For example, chemotherapeutic agents or other anti-proliferative agents may be combined with the compounds of this invention to treat proliferative diseases and cancer. Examples of known chemotherapeutic agents include, but are not limited to, For example, other therapies or anticancer agents that may be used in combination with the inventive anticancer agents of the present invention include surgery, radiotherapy (in but a few examples, gamma.-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide. For a more comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Other examples of agents the inhibitors of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In an alternate embodiment, the methods of this invention that utilize compositions that do not contain an additional therapeutic agent, comprise the additional step of separately administering to said patient an additional therapeutic agent. When these additional therapeutic agents are administered separately they may be administered to the patient prior to, sequentially with or following administration of the compositions of this invention.

The compounds of this invention or pharmaceutically acceptable compositions thereof may also be incorporated into compositions for coating implantable medical devices, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device.

Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting ROCK, ERK, GSK, or AGC (e.g., PKA, PDK, $p70^{S6K}$-1 and -2, and AKT) activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of ROCK, ERK, GSK, or AGC (e.g., PKA, PDK, $p70^{S6K}$-1 and -2, and AKT) kinase activity in a biological sample is useful for a variety of purposes that are known to one of skill in the art. Examples of such purposes include, but are not limited to, blood transfusion, organ-transplantation, biological specimen storage, and biological assays.

EXAMPLES

As depicted in the Examples below, in certain exemplary embodiments, compounds are prepared according to the following general procedures. It will be appreciated that although the general methods depict the synthesis of certain compounds of the present invention, the following general methods, in addition to the Schemes set forth below and other methods known to one of ordinary skill in the art, can be applied to all compounds and subclasses and species of each of these compounds, as described herein.

Unless otherwise indicated, each $^1$H NMR was obtained at 500 MHz and compound numbers correspond to those compound numbers recited in Table 1.

Example 1

5-Pyridin-4-yl-2H-[1,2,4]triazol-3-ylamine: Prepared according to the method described in Lipinski, C. A.; LaMattina, J. L.; Hohnke, L. A.; *J. Med. Chem.*, 1985, 28 (11), 1628-1636. FIA MS: [M+H]=162.3; $^1$H NMR $d_6$-DMSO: 12.4 (1H, br s), 8.6 (2H, s), 7.8 (2H, s), 6.3 (2H, s).

Example 2

5-Pyridin-4-yl-[1,3,4]oxadiazol-2-ylamine: Prepared as described in EP 641797. $^1$H NMR $d_6$-DMSO: 9.1 (d, 2H), 8.1 (d, 2H), 7.9 (br s, 2H).

Example 3

3-Pyridin-4-yl-[1,2,4]oxadiazol-5-ylamine: Prepared as described in EP 641797. $^1$H NMR $d_6$-DMSO: 8.75 (d, 2H), 8.10 (br s, 2H), 7.75 (d, 2H).

Example 4

5-Pyridin-4-yl-1H-imidazol-2-ylamine: Prepared as described in *J. Med. Chem.*, 38, 3342, 1995 $^1$H NMR $d_6$-DMSO: 8.6 (d, 2H), 7.8 (s, 1H), 7.7 (m, 2H), 7.5 (br s, 2H).

Example 5

N-(5-Pyridin-4-yl-1H-pyrazol-3-yl)-acetamide: To 3-oxo-3-pyridin-4-yl-propionitrile (10.0 g, 45 mmol) in 50 mL of acetic acid was added hydrazine monohydrate (1.59 g, 50 mmol) and the solution was heated to 70° C. overnight. The resulting white precipitate was collected and washed with diethyl ether and dried in vacuum to afford: 5.1 g (56% yield) of the title compound as an acetate salt. $^1$H NMR d6-DMSO: 10.90-10.60 (1H, vbs) 8.60-8.59 (2H, d), 7.71-7.70 (2H, d), 7.15-6.90 (1H, br s), 2.03 (3H, s), 1.87 (3H, s). FIA MS: MH$^+$203.1, M$^-$201.2.

Example 6

5-Pyridin-4-yl-1H-pyrazol-3-ylamine: N-(5-Pyridin-4-yl-1H-pyrazol-3-yl)-acetamide (4.1 g, 20.3 mmol) was heated in 6N HCl (30 mL) overnight. Solution was concentrated in vacuum to afford the title compound (3.82 g, 96% yield) as a white hydrochloride salt. $^1$H NMR ($d_6$-DMSO): 8.92-8.91 (2H, d), 8.43-8.42 (2H, d), 7.38-6.81 (1H, br s). FIA MS: MH$^+$161.2, M$^-$159.1.

Example 7

3-Pyridin-4-yl-isoxazol-5-ylamine: To 3-oxo-3-pyridin-4-yl-propionitrile (2.0 g, 13.7 mmol) in 20 mL of ethanol was added hydroxylamine hydrochloride (0.75 g, 10.8 mmol) and the resulting solution was heated at 70° C. overnight. The resulting white precipitate was collected and the solution was concentrated and dried in vacuum to afford the title compound (1.2 g, 54%) as a yellow solid. FIA MS: MH$^+$162.2, M$^-$160.0.

Example 8

Acylation of Amines, General Method A:

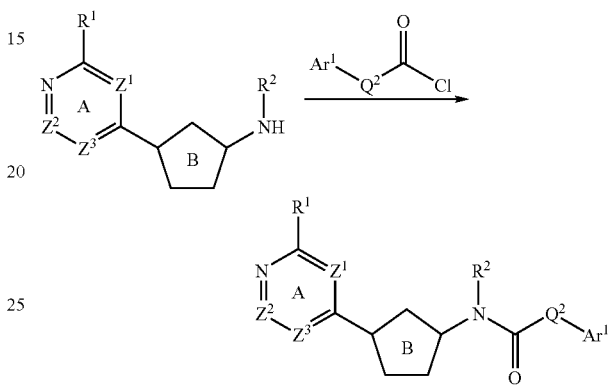

The amine and acid chloride, as depicted above, are combined in anhydrous DMF. Et$_3$N is then added to the reaction mixture, and the mixture stirred at ambient temperature. After completion of the reaction, EtOAc is added, the organic layer washed with H$_2$O and brine, then dried over Na$_2$SO$_4$. Removal of the solvent affords compounds of formula II wherein Q$^1$ is —C(O)—.

Acylation of Amines, General Method B:

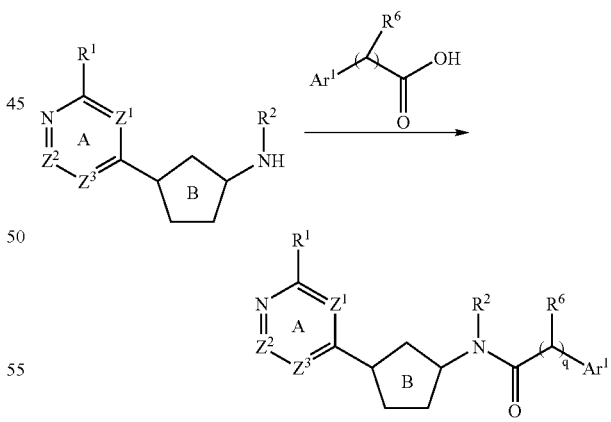

A mixture of BtSO$_2$CH$_3$ (preparation described below), the acid depicted above, and Et$_3$N is heated at in dry THF. The amine depicted above is then added to the reaction mixture, and the mixture heated at reflux. After the mixture is concentrated, an appropriate organic solvent is added, and the organic phase washed with 2 M NaOH and dried over anhydrous MgSO$_4$. Removal of the solvent affords a compound of formula V.

Acylation of Amines, General Method C:

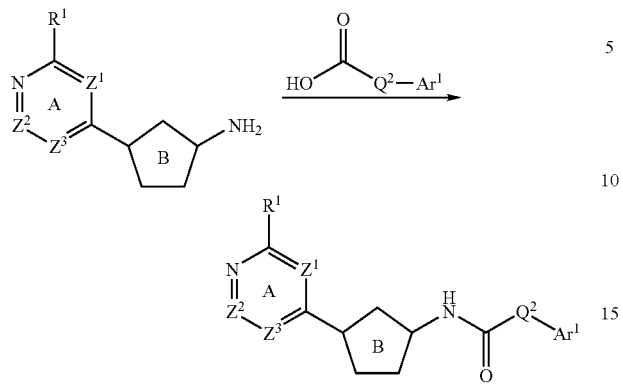

The amine and carboxylic acid, depicted above, and Bt-SO$_2$Me are combined in a microwave reaction vessel. Anhydrous THF is added followed by triethylamine and the mixture heated by microwave irradiation at 160° C. for 10 minutes. Isolation by precipitation or preparative HPLC affords a compound of formula II wherein R$^2$ is hydrogen and Q$^1$ is —C(O)—.

Example 9

One of skill in the art would recognize that a variety of protecting groups are suitable for the methods described herein. Amino and hydroxyl protecting groups, and removal thereof, are well known in the art and are described in detail in *Protecting Groups in Organic Synthesis*, Theodora W. Greene and Peter G. M. Wuts, 1991, published by John Wiley and Sons, the entirety of which is hereby incorporated by reference.

Protection of Amino Groups, General Method D:

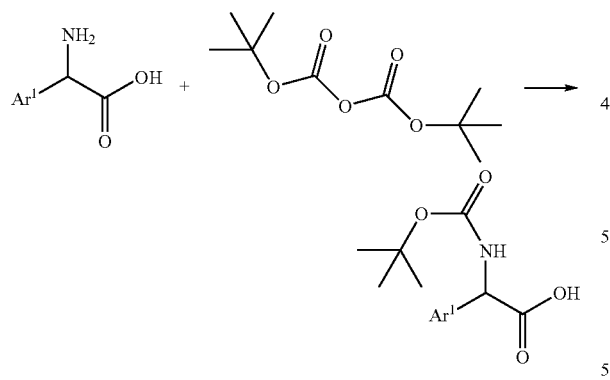

0.25 mmol of the amine depicted above, 0.25 mmol of Boc anhydride are mixed in 2 mL of anhydrous CH$_2$Cl$_2$. To the reaction mixture, 0.75 mmol of Et$_3$N is added and the mixture stirred at ambient temperature. The solvent is removed in vacuo to afford the Boc protected amine depicted above.

Deprotection of Boc-protected Amines, General Method E:

To the Boc protected amine (0.25 mmol) in a vial, 2 mL 4N HCl in dioxane is added and the reaction mixture stirred at ambient temperature for 30 minutes. The solvent is evaporated to afford the free amine product.

Protection of Phenols and Alcohols, General Method F:

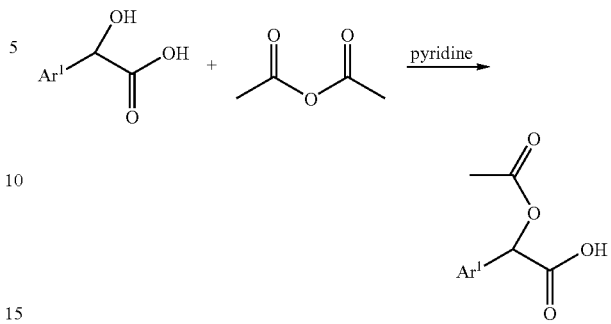

The hydroxy acid depicted above (2.5 mol) is stirred with acetic anhydride (0.57 mL, 6 mol) in pyridine (5 mL) overnight and then concentrated in vacuo. The resulting oil is partitioned between EtOAc and 1N HCl and the resulting organic layer washed successively with 1 N HCl, water and brine, dried over MgSO$_4$, and evaporated to dryness.

Deprotection of Acetylated Phenols and Alcohols, General Method G:

The acetyl-protected alcohol or phenol (0.25 mmol) is dissolved in EtOH, 0.5 mL 2N NaOH is added and the mixture stirred at ambient temperature for 1 hour. The solvent is evaporated and the resulting residue is subjected to preparative HPLC, or other methods, for purification.

Example 10

Preparation of Phenylacetic Acids, General Method H:

Substituted benzaldehyde (5 mmol) and zinc iodide (10 mg) were dissolved or suspended in anhydrous acetonitrile (5-10 mL). Trimethylsilyl cyanide (12 mmol) was added dropwise and the mixture stirred at room temperature overnight. The mixture was rotary evaporated and the residue dissolved in glacial acetic acid (2 mL) and concentrated hydrochloric acid (3 mL). Tin (II) chloride dihydrate (12 mmol) was added and the mixture heated to reflux for 1-2 hours. To the cooled mixture was added water (20 mL) and the mixture was extracted with methylene chloride (3×15 mL). The extracts were washed with water (×2) and brine and dried over MgSO$_4$. The solution is concentrated and the product precipitated by addition of hexane.

Preparation of α-hydroxyphenylacetic Acids, General Method I:

Substituted benzaldehyde (5 mmol) and zinc iodide (10 mg) were dissoved or suspended in anhydrous acetonitrile (5-10 mL). Trimethylsilyl cyanide (12 mmol) was added dropwise and the mixture stirred at room temperature overnight. The mixture was rotary evaporated and the residue dissolved in glacial acetic acid (2 mL) and concentrated hydrochloric acid (3 mL) and the mixture heated to reflux for 1-2 hours. To the cooled mixture was added water (20 mL) and the mixture was extracted with methylene chloride (3×15 mL). The extracts were washed with water (×2) and brine and dried over MgSO$_4$. The solution is concentrated and the product precipitated by addition of hexane.

Although the preparation of certain amines are described below, it will be appreciated that a variety of alternate amines can be prepared as described generally below and can be utilized in the preparation of compounds of the invention.

Example 11

N-(1-Methanesulfonyl)benzotriazole (BtSO$_2$CH$_3$): To an ice-cold solution of benzotriazole (11.9 g, 0.10 mol) and pyridine (12.0 g, 0.16 mol) in dry toluene (120 mL) was added methylsulfonyl chloride (9.3 mL, 0.12 mol) in toluene (30 mL) dropwise. The mixture was then stirred overnight at room temperature. EtOAc (150 mL) and H$_2$O (100 mL) were added, the organic layer was separated, successively washed with water and brine, and dried over anhydrous MgSO$_4$. Removal of solvents in vacuo afforded the title compound as a white solid.

Example 12

3-(3-chloro-propoxy)-phenylacetic acid:

Step A: Methyl 3-hydroxyphenylacetate (87 g, 0.52 mol) was dissolved in acetone (500 mL). 1-Bromo-3-chloropropane (55 mL, 0.56 mol) was added, followed by potassium carbonate (73 g, 0.53 mol) and acetone (100 mL). The reaction was heated at reflux. After 24 hours, more 1-bromo-3-chloropropane (5 mL, 50 mmol) was added and the reaction refluxed for a further 24 hours. The mixture was cooled, filtered and rotary evaporated. The product was purified by passage over a short column of silica gel (650 g: 135 mm diameter column) eluted with hexane, and 30% ethyl acetate in hexane, to afford methyl 3-(3-chloro-propoxy)-phenylacetate (120 g, 95%) as an oil. $^1$H NMR (CDCl$_3$) δ 7.25 (1H, dd), 6.93-6.85 (3H, m), 4.16 (2H, t), 3.79 (2H, t), 3.73 (3H, s), 3.62 (2H, s), 2.28 (2H, m).

Step B: Methyl 3-(3-chloro-propoxy)-phenylacetate (12.7 g, 52.3 mmol) was dissolved in dioxane (25 mL) and 1N NaOH (53 mL) was added. The mixture was stirred at room temperature for 45 minutes then acidified by addition of 1N hydrochloric acid (60 mL). A white precipitate formed which was filtered, washed with 1N HCl, water and dried. 3-(3-Chloro-propoxy)-phenylacetic acid (11.7 g, 98%). $^1$H NMR (CDCl$_3$) δ 7.25 (1H, dd), 6.93-6.85 (3H, m), 4.11 (2H, t), 3.79 (2H, t), 3.70 (2H, s), 2.25 (2H, m).

Example 13

3-(2-chloro-ethoxy)-phenylacetic acid:

Step A: Methyl 3-hydroxyphenylacetate (10.8 g, 65 mmol) was dissolved in acetone (120 mL). 1-Bromo-2-chloroethane (5.5 mL, 66 mmol) was added, followed by potassium carbonate (10.1 g, 73.6 mmol). The reaction was heated at reflux. After 24 hours, more 1-bromo-2-chloroethane (11 mL, 132 mmol) was added and the reaction refluxed for a further 24 hours. The mixture was cooled, filtered and rotary evaporated. The product was purified by passage over a short column of silica gel eluted with hexane, and 30% ethyl acetate in hexane, to afford methyl 3-(3-chloroethoxy)-phenylacetate as an oil.

Step B: Methyl 3-(2-chloro-ethoxy)-phenylacetate (7.0 g, 32.9 mmol) was dissolved in methanol (40 mL) and 6N NaOH (5.5 mL) was added. The mixture was stirred at room temperature overnight then acidified by addition of 6N hydrochloric acid (5.5 mL). A white precipitate formed which was filtered, washed with 1N HCl, water and dried to afford 3-(2-chloroethoxy)-phenylacetic acid (6.5 g, 99%). $^1$H NMR (CDCl$_3$) δ3.55 (s, 2H), 3.75 (t, 2H), 4.15 (t, 2H), 6.78 (dd, 1H), 6.80 (d, 1H), 6.84 (dd, 1H), 7.16 (dd, 1H).

Example 14

3-Ethoxyphenylacetic acid:

Step A: Methyl 3-hydroxyphenylacetate (6.4 g, 38.5 mmol) was dissolved in acetone (50 mL). Ethyl bromide (3.5 mL, 46.9 mmol) was added, followed by potassium carbonate (6.37 g, 46 mmol) and the resulting reaction mixture was heated at reflux. After 24 hours, more ethyl bromide (3.55 mL, 46.9 mmol) was added and the reaction refluxed for a further 24 hours. The mixture was cooled, filtered and rotary evaporated. The product was dissolved in ethyl acetate and the solution washed with saturated sodium bicarbonate (2×50 mL) and brine, and dried (MgSO$_4$). Removal of solvent revealed methyl 3-ethoxyphenylacetate as an oil that crystallized upon standing. $^1$H NMR (CDCl$_3$) δ 7.25 (1H, dd), 6.87 (3H, m), 4.08 (2H, q), 3.73 (3H, s), 3.65 (2H, s), 1.45 (3H, t).

Step B: Methyl 3-ethoxyphenylacetate (7.5 g, 38.6 mmol) was dissolved in ethanol (15 mL) and 1N NaOH (40 mL) was added. The mixture was stirred at room temperature for 30 minutes then acidified by addition of 1N hydrochloric acid (45 mL). A white precipitate formed which was filtered, washed with 1N HCl, water and dried to afford 3-ethoxyphenylacetic acid (6.4 g, 92%). $^1$H NMR (CDCl$_3$) δ 7.20 (1H, dd), 6.8 (3H, m), 4.0 (2H, q), 3.6 (2H, s), 1.4 (3H, t).

Example 15

3-(Methanesulfonylamino)phenylacetic acid:

Step A: 3-Aminophenylacetic acid (15.5 g, 0.10 mol) was suspended in methanol (150 mL) and cooled to 0° C. Thionyl chloride (11.2 mL, 0.15 mol) was added dropwise while stirring. A clear orange solution was obtained, which was stirred for 4 hours, then evaporated. The solid residue was partitioned between ethyl acetate (150 mL) and saturated sodium bicarbonate (150 mL) and the organic phase washed with saturated sodium bicarbonate (100 mL), and brine and dried (Na$_2$SO$_4$) to afford methyl 3-aminophenylacetate as a brown oil. (14.1 g, 83%). $^1$H NMR (CDCl$_3$) δ 7.12 (1H, dd), 6.7-6.6 (3H, m), 3.71 (3H, s), 3.55 (2H, s).

Step B: Methyl 3-aminophenylacetate (2.26 g, 13.7 mmol) was dissolved in dry methylene chloride (20 mL) and cooled to 0° C. Pyridine (2.2 mL, 27.2 mmol) was added followed by dropwise addition of methanesulfonyl chloride (1.3 mL, 16.8 mmol). The mixture was stirred at 0° C. for 1 hour and at room temperature for 3 hours, then poured into 100 mL of saturated sodium bicarbonate solution. The organic layer was washed with saturated sodium bicarbonate (100 mL), 1N HCl (2×100 mL) and brine. Dried over MgSO$_4$. Solvent was evaporated to afford methyl 3-(methanesulfonylamino)phenylacetate. (3.36 g, 100%). $^1$H NMR (CDCl$_3$) δ 7.32 (1H, dd), 7.2-7.1 (3H, m), 6.57 (1H, s), 3.72 (3H, s), 3.64 (2H, s), 3.02 (3H, s).

Step C: Methyl 3-(methanesulfonylamino)phenylacetate (3.36 g, 13.8 mmol) was dissolved in ethanol (16 mL) and 1N NaOH (30 mL) added. The reaction was stirred for 1 hour, then 1N HCl (50 mL) and water (50 mL) were added. The product was extracted into ethyl acetate (3×50 mL) and the combined extracts were washed with water and brine and dried (MgSO$_4$). Removal of solvent afforded 3-(methanesulfonylamino)phenylacetic acid (2.90 g, 92%). $^1$H NMR (DMSO-$_6$) δ 12.32 (1H, br), 9.69 (1H, br), 7.26 (1H, dd), 7.10 (2H, m), 7.00 (1H, d), 6.57 (1H, s), 3.54 (2H, s), 2.97 (3H, s).

Example 16

(3-Ethylsulfamoyl-phenyl)-acetic acid:
Step A: 2-(3-Mercaptophenyl)acetic acid (1.0 g, 6.0 mmol) was dissolved in dry methanol (40 mL). To this solution 10 drops concentrated sulfuric acid was added and the reaction mixture was heated to reflux for 36 hours. The reaction mixture was then concentrated to about half the volume, diluted with ethyl acetate, and the organic layer washed with saturated sodium bicarbonate solution. The organic layer was dried over sodium sulfate and concentrated to afford methyl 2-(3-mercaptophenyl)acetate as an oil (0.55 g, 3.0 mmol, 50% yield). $^1$H NMR (CDCl$_3$) 7.05 ppm, 3H, m; 6.88 ppm, 1H, m; 3.53 ppm, 3H, s; 3.38 ppm, 2H, s.

Step B: Methyl 2-(3-mercaptophenyl)acetate (0.55 g, 3.0 mmol) was dissolved in 10 mL acetonitrile and potassium nitrate (0.76 g, 7.5 mmol) was added and the reaction mixture cooled to 0° C. To this suspension sulfuryl chloride was added (0.6 mL, 7.5 mmol) at 0° C. and the reaction mixture was let warm to room temperature and stirred overnight. A solution of saturated sodium bicarbonate was added followed by ethyl acetate (100 mL each). The organic layer was washed with brine, dried over sodium sulfate and concentrated to afford methyl 2-(3-chlorosulfonylphenyl)acetate as an oil (0.59 g, 2.4 mmol, 79% yield). $^1$H NMR (CDCl$_3$) 7.91 ppm, 2H, m; 7.60 ppm, 1H, d; 7.53 ppm, 1H, t; 3.73 ppm, 2H, s; 3.72 ppm, 3H, s.

Step C: Methyl 2-(3-chlorosulfonyl-phenyl)acetate (0.29 g, 1.17 mmol) was dissolved in THF (10 mL) and to this solution 1 mL (2 mmol) of 2M ethylamine in THF was added. Let stir at room temperature 30 minutes, diluted with ethyl acetate and the organic layer was washed with 10% citric acid, brine, dried over sodium sulfate and concentrated to afford (3-ethylsulfamoyl-phenyl)-acetic acid methyl ester as an oil (0.28 g, 1.09 mmol, 93% yield). $^1$H NMR (CDCl$_3$) 7.72 ppm, 2H, m; 7.41 ppm, 2H, m; 4.32 ppm, 1H, t; 3.68 ppm, 3H, s; 3.67 ppm, 2H, s; 2.98 ppm, 2H, m; 1.07 ppm, 3H, t.

Step D: (3-Ethylsulfamoyl-phenyl)-acetic acid methyl ester (0.28 g, 1.1 mmol) was dissolved in THF and LiOH hydrate (63 mg, 1.5 mmol) in water was added. The reaction mixture was stirred at room temperature for 4 hours and then diluted with ethyl acetate and 10% citric acid. The organic layer was washed with brine, dried over sodium sulfate, and concentrated to afford (3-ethylsulfamoyl-phenyl)-acetic acid as a solid (0.25 g, 1.1 mmol 99% yield). $^1$H NMR (DMSO-d$_6$) 7.71 ppm, 1H, s; 7.70 ppm, 1H, m; 7.50 ppm, 3H, m; 4.11 ppm, 1H, br s; 3.70 ppm, 2H, s; 2.81 ppm, 2H, m; 0.99 ppm, 3H, t.

Example 17

3-(3-(N-Boc-piperidin-4-yl)-propoxy)-phenylacetic acid:

Step A: 4-Pyridinepropanol (10.0 g, 73 mmol) was dissolved in glacial acetic acid (50 mL). 10% Palladium on carbon (1.1 g) was added and the mixture hydrogenated under 50 psi hydrogen gas for 6 days. The mixture was filtered through Celite® and the solvent removed by rotary evaporation. The crude product 3-piperidin-4-yl-propan-1-ol (acetic acid salt) was used as obtained. $^1$H NMR (CDCl$_3$) δ 6.3 (br), 3.65 (2H, t), 3.36 (2H, m), 2.79 (2H, dt), 2.01 (3H, s), 1.85 (2H, m), 1.7-1.3 (7H, m).

Step B: The crude 3-piperidin-4-yl-propan-1-ol (73 mmol) was dissolved in dioxane (100 mL) and 3N NaOH (25 mL) was added to give a pH9 solution. Di-tert-butyl dicarbonate (16.0 g, 73 mmol) in dioxane (35 mL) was added dropwise, with simultaneous addition of 3N NaOH to maintain the solution at approximately pH 9. After 2 hours no residual amine was visible by TLC analysis (ninhydrin stain) and the reaction was diluted with water (200 mL)and extracted with ethyl acetate (3×100 mL). The combined extracts were washed with water and brine and dried (MgSO$_4$). Removal of solvent afforded 20 g crude product which was purified by silica gel chromatography (200 g silica) in a sintered glass funnel (L. M. Harwood, Aldrichimica Acta, 1985, 18, 25) eluted with 500 mL each of hexane, 20%, 40%, 60% and 80% ethyl acetate in hexane to afford 3-(N-Boc-piperidin-4-yl)-propan-1-ol as a clear, colorless oil (14.5 g, 82%). $^1$H NMR (CDCl$_3$) δ 4.09 (2H, m), 3.66 (2H, t), 2.69 (2H, dt), 1.7-1.5 (4H, m), 1.47 (9H, s), 1.4-1.3 (5H, m), 1.12 (2H, m).

Step C: 3-Hydroxyphenylacetic acid (75.3 g, 0.5 mol) was dissolved in methanol (900 mL). Concentrated sulfuric acid (2 mL) was added and the mixture refluxed for 5 hours. The solvent was evaporated and the residue dissolved in ethyl acetate (1000 mL) and washed with water (2×600 mL), brine, and dried (MgSO$_4$). Solvent was evaporated to afford methyl 3-hydroxyphenylacetate as an oil (82 g, quantitative yield). $^1$H NMR (CDCl$_3$) δ 7.2 (1H, t), 6.9-6.75 (3H, m), 5.5 (1H, br), 3.75 (3H, s), 3.63 (2H, s).

Step D: To a solution of methyl 3-hydroxyphenylacetate (0.409 g, 2.4 mmol), 3-(N-Boc-piperidin-4-yl)-propan-1-ol (0.50 g, 20.5 mmol) and triphenylphosphine (0.645, 24.6 mmol) in THF, was added diisopropyl azodicarboxylate at 0° C. slowly, then the ice bath was removed and the reaction mixture was stirred at room temperature overnight. The solvent was removed and the residue was dissolved in methylene chloride (2 mL) and loaded on a silica gel column. The product was eluted with 20% ethyl acetate in hexane, to afford methyl 3-(3-(N-Boc-piperidin-4-yl)-propoxy)-phenylacetate (0.5 g, 62%). $^1$H NMR (CDCl$_3$) δ1.1 (m, 2H), 1.4 (m, 2H), 1.46 (s, 9H), 1.66 (d, 2H), 1.78 (m, 2H), 2.67 (t, 2H), 3.58 (s, 2H), 3.68 (s, 3H), 4.05 (m, 2H), 6.75 (m, 3H), 7.18 (dd, 1H).

Step E: Methyl 3-(3-(N-Boc-piperidin-4-yl)-propoxy)-phenylacetate (0.5 g, 1.3 mmol) was dissolved in methanol and 2N NaOH (3 mL) added. The reaction was stirred at 60° C. for 2 hours then the solution was adjusted to pH 6.5. The product was extracted into ethyl acetate, and the organic phase was dried by MgSO$_4$. The solvent was evaporated to afford 3-(3-(N-Boc-piperidin-4-yl)-propoxy)-phenylacetic acid (0.30 g). $^1$H NMR (CDCl$_3$) δ 1.02 (m, 2H), 1.25 (m, 2H), 1.55 (m, 2H), 1.65 (m, 2H), 2.57 (m, 2H), 3.33 (m, 1H), 3.75 (s, 2H), 3.95 (m, 2H), 6.63 (m, 3H), 6.98 (m, 1H).

Example 18

Compounds of the present invention were prepared by methods substantially similar to those described herein. Certain compounds of the present invention are prepared by the acylation of the amines prepared as set forth at Examples 1, 2, 3, and 5 above. These amines were acylated with a variety of the phenyl acetic acids described herein using the general methods are set forth below.

Acylation of 5-Pyridin-4-yl-2H-[1,2,4]triazol-3-ylamine: A solution of 5-pyridin-4-yl-2H-[1,2,4]triazol-3-ylamine (0.5 mmol) and Et$_3$N (3 mmol) in THF (4 ml) was cooled to 0° C., and acid chloride (1.2 mmol) added. The mixture was allowed to warm to room temperature and stirred for 16 hr. The mixture was then concentrated in vacuo, partitioned between methylene chloride and water and the organic layer washed twice more with water. The organic layer was then evaporated to dryness and the product recrystallised from methanol. If necessary the product was further purified by preparative HPLC.

Acylation of 5-Pyridin-4-yl-[1,3,4]oxadiazol-2-ylamine: A solution of 5-pyridin-4-yl-[1,3,4]oxadiazol-2-ylamine (0.5 mmol) in pyridine (4 ml) was cooled to 0° C., and acid chloride (1.0 mmol) added. The mixture was stirred for 16 hours at 55° C. The mixture was then evaporated to dryness and partitioned between ethyl acetate and water and the organic layer washed twice more with water. In some cases the product precipitated out pure from the ethyl acetate layer and was filtered off, washed and dried. In the remaining cases, the organic layer was evaporated to dryness and the product purified by preparative HPLC.

Acylation of 5-Pyridin-4-yl-2H-pyrazol-3-ylamine: A solution of 5-pyridin-4-yl-2H-pyrazol-3-ylamine (0.5 mmol) in pyridine (4 ml) was cooled to 0° C., and acid chloride (1.0 mmol) added. The mixture was stirred for 16 h at or at 55° C. The mixture was then evaporated to dryness and partitioned between ethyl acetate and water and the organic layer washed twice more with water. In some cases the product precipitated out pure from the ethyl acetate layer and was filtered off, washed and dried. In the remaining cases, the organic layer was evaporated to dryness and the product purified by preparative HPLC.

Acylation of 3-Pyridin-4-yl-[1,2,4]oxadiazol-5-ylamine: To a solution of 3-pyridin-4-yl-[1,2,4]oxadiazol-5-ylamine (0.5 mmol) in pyridine (4 ml) was added 0.6 mmol of 2-tert-butylimino-2-diethylamino-1,3-dimethylperhydro-1,3,2-diazaphosphorine (BEMP) and the mixture stirred at room temperature for 1 hr. The mixture was then cooled to 0° C. and the acid chloride (1.0 mmol) added. The mixture was heated at reflux overnight, and then evaporated to dryness. The crude product was partitioned between ethyl acetate and water and the organic layer washed twice more with water. The organic layer was then evaporated to dryness and the product purified by preparative HPLC.

Example 19

Compounds of the present invention were prepared by methods substantially similar to those described in the above Examples 1-19 and those known in the art. The characterization data for these compounds is summarized in Table 2 below and includes mass spectral data, HPLC retention time, and $^1$H NMR data. Compound numbers in Table 2 correspond to the compound numbers listed in Table 1.

As used herein, the term $R_t$ refers to the retention time, in minutes, obtained for the compound using the HPLC method designated.

Unless otherwise indicated, the HPLC method designated "A" relates to the following HPLC method:
Column: Hypersil BDS C18 5 μm, 2.1×50 mm
Flow rate: 1.0 mL/minute
Gradient: 0-95% CH$_3$CN (0.1% TFA) in H$_2$O (0.1% TFA) over 2.39 minutes Unless otherwise indicated, the HPLC method designated "B" relates to the following HPLC method:
Column: Hypersil BDS C18 5 μm, 2.1×50 mm
Flow rate: 1.0 mL/minute
Gradient: 15-90% CH$_3$CN (0.1% TFA) in H$_2$O (0.1% TFA) over 2.39 minutes

TABLE 2

Characterization Data for Selected Compounds of Formula I

| Compound No | M + 1 | $R_t$ | HPLC Method | $^1$H NMR (500 MHz) |
|---|---|---|---|---|
| I-1 | 279 | 1.34 | A | — |
| I-2 | 339 | 1.31 | A | — |
| I-3 | 339 | 1.43 | A | — |
| I-4 | 309 | 1.37 | A | — |
| I-5 | 313 | 1.48 | A | — |
| I-6 | 329 | 1.48 | A | — |
| I-7 | 357 | 1.41 | A | — |
| I-8 | 329 | 1.52 | A | — |
| I-9 | 309 | 1.41 | A | — |
| I-10 | 331.06 | 1.74 | B | DMSO-d$_6$: 10.90(1H, bs), 8.76-8.74(2H, m), 8.10-7.90(2H, bs), 7.57-7.55(H, m), 7.39-7.34(3H, m), 3.67(2H, s) |
| I-11 | 297.13 | 1.33 | B | DMSO-d$_6$: 11.00-10.90(1H, bs), 8.76-8.75(2H, m), 8.10-7.90(2H, bs), 7.38-7.35(2H, m), 7.18-7.14(2H, m), 3.67(2H, s) |
| I-12 | 293.17 | 1.48 | B | DMSO-d$_6$: 10.72(1H, bs), 8.80-8.78(2H, m), 8.10(2H, bs), 7.30-7.17(6H, m), 2.83-2.90(2H, m), 2.68-63(2H, m) |
| I-13 | 358 | 1.7 | A | — |
| I-14 | 330 | 1.76 | A | — |
| I-15 | 340 | 1.53 | A | — |
| I-16 | 310 | 1.62 | A | — |
| I-17 | 340 | 1.39 | A | — |
| I-18 | 330 | 1.19 | A | — |
| I-19 | 332.1 | 2.15 | B | DMSO-d$_6$: 14.00(1H, bs), 12.08(1H, bs), 8.79-8.78(2H, d), 8.08-8.06(2H, d), 7.42-7.40(1H, d), 7.38-7.34(2H, m), 3.81(2H, s) |
| I-20 | 298.1 | 1.7 | B | DMSO-d$_6$: 13.99(1H, bs), 12.07(1H, bs), 8.79-8.78(2H, d), 8.08-8.07(2H, d), 7.40-7.37(2H, d), 7.20-7.15(2H, d), 3.77(2H, s) |
| I-21 | 281 | 1 | A | 3.71(2H, s), 7.24(5H, m), 7.75(2H, m), 8.72(2H, m), 12.15(1H, s) |
| I-22 | 341 | 1.01 | A | — |
| I-23 | 315 | 1.48 | A | — |
| I-24 | 311 | 1 | A | — |
| I-25 | 299 | 1.02 | A | — |
| I-26 | 359 | 1.07 | A | — |
| I-27 | 331 | 1.5 | A | — |
| I-28 | 311 | 1.33 | A | — |
| I-29 | 331 | 1.5 | A | — |
| I-30 | 281 | 1.36 | A | — |
| I-31 | 341 | 1.41 | A | — |
| I-32 | 311 | 1.4 | A | — |
| I-33 | 311 | 1.41 | A | — |
| I-34 | 331 | 1.55 | A | — |
| I-35 | 299 | 1.43 | A | — |
| I-36 | 360 | 1.43 | A | — |
| I-37 | 331 | 1.52 | A | — |

Example 20

ROCK Inhibition Assay

Compounds were screened for their ability to inhibit ROCK I (AA 6-553) activity using a standard coupled enzyme system (Fox et al. (1998) *Protein Sci.* 7, 2249). Reactions were carried out in a solution containing 100 mM HEPES (pH 7.5), 10 mM MgCl$_2$, 25 mM NaCl, 2 mM DTT and 1.5% DMSO. Final substrate concentrations in the assay were 45 μM ATP (Sigma Chemicals, St Louis, Mo.) and 200 μM peptide (American Peptide, Sunnyvale, Calif.). Reactions were carried out at 30° C. and 45 nM ROCK I. Final concentrations of the components of the coupled enzyme system were 2.5 mM phosphoenolpyruvate, 350 μM NADH, 30 μg/ml pyruvate kinase and 10 μg/ml lactate dehydrogenase.

Compounds of the invention were found to inhibit ROCK.

Example 21

ERK Inhibition Assay

Compounds were assayed for the inhibition of ERK2 by a spectrophotometric coupled-enzyme assay (Fox et al (1998) *Protein Sci* 7, 2249). In this assay, a fixed concentration of activated ERK2 (10 nM) was incubated with various concentrations of the compound in DMSO (2.5%) for 10 min. at 30° C. in 0.1 M HEPES buffer, pH 7.5, containing 10 mM $MgCl_2$, 2.5 mM phosphoenolpyruvate, 200 μM NADH, 150 μg/mL pyruvate kinase, 50 μg/mL lactate dehydrogenase, and 200 μM erktide peptide. The reaction was initiated by the addition of 65 μM ATP. The rate of decrease of absorbance at 340 nM was monitored. The $K_i$ was determined from the rate data as a function of inhibitor concentration.

Compounds of the invention were found to inhibit ERK2.

Example 22

GSK Inhibition Assay

Compounds were screened for their ability to inhibit GSK-3β (AA 1-420) activity using a standard coupled enzyme system (Fox et al. (1998) *Protein Sci.* 7, 2249). Reactions were carried out in a solution containing 100 mM HEPES (pH 7.5), 10 mM $MgCl_2$, 25 mM NaCl, 300 μM NADH, 1 mM DTT and 1.5% DMSO. Final substrate concentrations in the assay were 20 μM ATP (Sigma Chemicals, St Louis, Mo.) and 300 μM peptide (American Peptide, Sunnyvale, Calif.). Reactions were carried out at 30° C. and 20 nM GSK-3β. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above with the exception of ATP and the test compound of interest. The assay stock buffer solution (175 μl) was incubated in a 96 well plate with 5 μl of the test compound of interest at final concentrations spanning 0.002 μM to 30 μM at 30° C. for 10 min. Typically, a 12 point titration was conducted by preparing serial dilutions (from 10 mM compound stocks) with DMSO of the test compounds in daughter plates. The reaction was initiated by the addition of 20 μl of ATP (final concentration 20 μM). Rates of reaction were obtained using a Molecular Devices Spectramax plate reader (Sunnyvale, Calif.) over 10 min at 30° C. The $K_i$ values were determined from the rate data as a function of inhibitor concentration.

Compounds of the invention were found to inhibit GSK3

Example 23

PKA Inhibition Assay

Compounds were screened for their ability to inhibit PKA using a standard coupled enzyme assay (Fox et al., *Protein Sci*, 1998, 7, 2249). Assays were carried out in a mixture of 100 mM HEPES (pH 7.5), 10 mM $MgCl_2$, 25 mM NaCl, 1 mM DTT and 3% DMSO. Final substrate concentrations in the assay were 50 μM ATP (Sigma Chemicals) and 80 μM peptide (Kemptide, American Peptide, Sunnyvale, Calif.). Assays were carried out at 30° C. and 18 nM PKA. Final concentrations of the components of the coupled enzyme system were 2.5 mM phosphoenolpyruvate, 300 μM NADH, 30 μg/ml pyruvate kinase and 10 μg/ml lactate dehydrogenase.

An assay stock buffer solution was prepared containing all of the reagents listed above, with the exception of ATP, and the test compound of the present invention. 55 μl of the stock solution was placed in a 96 well plate followed by addition of 2 μl of DMSO stock containing serial dilutions of the test compound of the present invention (typically starting from a final concentration of 5 μM). The plate was preincubated for 10 minutes at 30° C. and the reaction initiated by addition of 5 μl of ATP (final concentration 50 μM). Initial reaction rates were determined with a Molecular Devices SpectraMax Plus plate reader over a 15 minute time course. $IC_{50}$ and $K_i$ data were calculated from non-linear regression analysis using the Prism software package (GraphPad Prism version 3.0a for Macintosh, GraphPad Software, San Diego Calif., USA).

Compounds of the present invention were found to inhibit PKA.

The invention claimed is:

1. A compound of formula V-A':

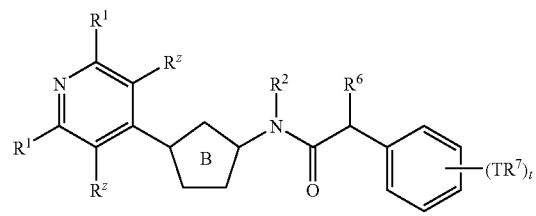

V-A' or a pharmaceutically acceptable salt thereof, wherein:

Ring B is a 5-membered heteroaryl ring selected from pyrazole, triazole, or oxadiazole, wherein Ring B is optionally substituted with 0-3 $R^4$ groups;

$R^Z$ is halogen, CN, $NO_2$, or $U_{(n)}R'$;

each $R^1$ is independently halogen, CN, $NO_2$, or $V_{(m)}R$;

V is an optionally substituted $C_{1-6}$ alkylidene chain, wherein up to two methylene units of the chain are optionally and independently replaced by —S—, —O—, —CS—, —$CO_2$—, —OC(O)—, —C(O)—, —C(O)C(O)—, —C(O)NR—, —$SO_2$NR—, —C(O)NRNR—, —OC(O)NR—, —S(O)—, or —$SO_2$—;

$R^2$ is $U_{(n)}R'$;

each occurrence of $R^4$ is independently halogen, CN, $NO_2$, or $U_{(n)}R$;

each occurrence of U is independently an optionally substituted $C_{1-6}$ alkylidene chain, wherein up to two methylene units of the chain are optionally and independently replaced by —NR—, —S—, —O—, —CS—, —$CO_2$—, —OC(O)—, —C(O)—, —C(O)C(O)—, —C(O)NR—, —NRC(O)—, —$NRCO_2$—, —$SO_2$NR—, —$NRSO_2$—, —C(O)NRNR—, —NRC(O)NR—, —OC(O)NR—, —NRNR—, —$NRSO_2$NR—, —S(O)—, or —$SO_2$—;

m and n are each independently 0 or 1;

each occurrence of R is independently hydrogen or an optionally substituted $C_{1-6}$ aliphatic group;

each occurrence of R' is independently hydrogen or an optionally substituted $C_{1-6}$ aliphatic group, a 3-8-membered saturated, partially unsaturated, or fully unsaturated monocyclic ring having 0-4 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; or: R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;

q is 0, 1, 2, or 3;

each occurrence of $R^6$ is independently halogen, CN, $NO_2$, or $U_{(n)}R'$, or: two occurrences of $R^6$, or R' and $R^6$, taken together with the atoms to which they are bound, form an optionally substituted 3-6-membered cycloalkyl, heterocyclyl, aryl or heteroaryl ring;

$Ar^1$ is a 5-8 membered saturated, partially unsaturated, or fully unsaturated monocyclic ring having 0-4 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur; wherein $Ar^1$ is optionally substituted with 0-5 occurrences of $TR^7$;

T is a valence bond or is a $C_1$-$C_6$ alkylidene chain wherein up to two methylene units of T are optionally and independently replaced by —NR—, —S—, —O—, —CS—, —$CO_2$—, —OC(O)—, —C(O)—, —C(O)C(O)—, —C(O)NR—, —NRC(O)—, —$NRCO_2$—, —$SO_2$NR—, —$NRSO_2$—, —C(O)NRNR—, —NRC(O)NR—, —OC(O)NR—, —NRNR—, —$NRSO_2$NR—, —S(O)—, or —$SO_2$—; and each occurrence of $R^7$ is independently R', halogen, $NO_2$, or CN, wherein optional substituents on an unsaturated carbon of an aryl or heteroaryl group are selected from halogen; $R°$; $OR°$; $SR°$; 1,2-methylene-dioxy; 1,2-ethylenedioxy; phenyl, optionally substituted with $R°$; —O(phenyl) optionally substituted with $R°$; $(CH_2)_{1-2}$(phenyl), optionally substituted with $R°$; CH=CH(phenyl), optionally substituted with $R°$; $NO_2$; CN; $N(R°)_2$; $NR°C(O)R°$; $NR°C(O)N(R°)_2$; $NR°CO_2R°$; —$NR°NR°C(O)R°$; $NR°NR°C(O)N(R°)_2$; $NR°NR°CO_2R°$; $C(O)C(O)R°$; $C(O)CH_2C(O)R°$; $CO_2R°$; $C(O)R°$; $C(O)N(R°)_2$; $OC(O)N(R°)_2$; $S(O)_2R°$; $SO_2N(R°)_2$; $S(O)R°$; $NR°SO_2N(R°)_2$; $NR°SO_2R°$; C(=S)$N(R°)_2$; C(=NH)—$N(R°)_2$; or $(CH_2)_{0-2}NHC(O)R°$, wherein each independent occurrence of $R°$ is selected from hydrogen, optionally substituted $C_{1-6}$ aliphatic, an unsubstituted 5-6 membered heteroaryl or heterocyclic ring, phenyl, O(phenyl), or $CH_2$(phenyl), or, notwithstanding the definition above, two independent occurrences of $R°$, on the same substituent or different substituents, taken together with the atom(s) to which each $R°$ group is bound, form a 3-8 membered cycloalkyl, heterocyclyl, aryl, or heteroaryl ring having 0-4 heteroatoms independently selected from nitrogen, oxygen, or sulfur, wherein optional substituents on the aliphatic group of $R°$ are selected from $NH_2$, $NH(C_{1-4}$aliphatic), $N(C_{1-4}$aliphatic$)_2$, halogen, $C_{1-4}$aliphatic, OH, $O(C_{1-4}$ aliphatic), $NO_2$, CN, $CO_2H$, $CO_2(C_{1-4}$aliphatic), O(halo$C_{1-4}$ aliphatic), or halo$C_{1-4}$aliphatic, optional substituents on an aliphatic group or on a non-aromatic heterocyclic ring are selected from those defined above for the unsaturated carbon of an aryl or heteroaryl group and the following: =O, =S, =NNHR* =NN(R*)$_2$, =NNHC(O)R* =$NNHCO_2$(alkyl), =$NNHSO_2$(alkyl), or =NR* where each R* is independently selected from hydrogen or an optionally substituted $C_{1-6}$ aliphatic, wherein substituents on the aliphatic group of R* are selected from $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic), and optional substituents on the nitrogen of a non-aromatic heterocyclic ring are selected from $R^+$, $N(R^+)_2$, $C(O)R^+$, $CO_2R^+$, $C(O)C(O)R^+$, $C(O)CH_2C(O)R^+$, $SO_2R^+$, $SO_2N(R^+)_2$, C(=S)$N(R^+)_2$, C(=NH)—$N(R^+)_2$, or $NR^+SO_2R^+$, wherein $R^+$ is hydrogen, an optionally substituted $C_{1-6}$ aliphatic, optionally substituted phenyl, optionally substituted O(phenyl), optionally substituted $CH_2$(phenyl), optionally substituted $(CH_2)_{1-2}$(phenyl), optionally substituted CH=CH(phenyl), or an unsubstituted 5-6 membered heteroaryl or heterocyclic ring having one to four heteroatoms independently selected from oxygen, nitrogen, or sulfur, or, notwithstanding the definition above, two independent occurrences of $R^+$, on the same substituent or different substituents, taken together with the atom(s) to which each $R^+$ group is bound, form a 3-8-membered cycloalkyl, heterocyclyl, aryl, or heteroaryl ring having 0-4 heteroatoms independently selected from nitrogen, oxygen, or sulfur, wherein optional substituents on the aliphatic group or the phenyl ring of $R^+$ are selected from $NH_2$, $NH(C_{1-4}$ aliphatic), $N(C_{1-4}$ aliphatic$)_2$, halogen, $C_{1-4}$ aliphatic, OH, $O(C_{1-4}$ aliphatic), $NO_2$, CN, $CO_2H$, $CO_2(C_{1-4}$ aliphatic), O(halo $C_{1-4}$ aliphatic), or halo($C_{1-4}$ aliphatic).

2. The compound according to claim 1, wherein:

each occurrence of $R^1$ is optionally substituted $C_1$-$C_4$aliphatic, OH, OR, SR, or $N(R)_2$;

each $R^2$ is independently hydrogen, or is $U_{(n)}R'$, where n is 1, and U is —$CH_2$—, —$CH_2CH_2$—, —$CH_2CH_2CH_2$—, —$CH_2CH_2CH_2CH_2$—, —$CH_2O$—, —$CH_2S$—, —$CH_2NR$—, —$CH_2CH_2O$—, —$CH_2CH_2S$—, —$CH_2CH_2NR$—, —$CH_2CH_2CH_2O$—, —$CH_2CH_2CH_2S$—, —$CH_2CH_2CH_2NR$—, —$CH_2CH_2CH_2CH_2O$—, —$CH_2CH_2CH_2CH_2S$—, —$CH_2CH_2CH_2CH_2NR$—, —$CH_2CH_2OCH_2CH_2$—, —$(CH_2)_4NHCH_2$—, —$(CH_2)_3NHCH_2CH_2$—, or —$CH_2CH_2NHCH_2CH_2$—, each R' is independently hydrogen, $C_1$-$C_4$alkyl, an optionally substituted group selected from tetrahydropyranyl, pyrrolidinyl, piperidinyl, piperazinyl, morpholinyl, thiomorpholinyl, pyridinyl, imidazolyl, phenyl, or cyclohexyl, or: R and R', taken together with the nitrogen atom to which they are bound, form an optionally substituted 5- or 6-membered saturated, partially unsaturated, or unsaturated heterocyclyl ring;

each occurrence of $R^4$ is independently hydrogen, $C_{1-6}$aliphatic, CN, C(O)R, C(O)OR, $C(O)N(R)_2$, or halogen;

each q is independently 1, 2, or 3; and each $R^6$ is independently R', —N(R)(R'), —$(CH_2)_{1-4}N(R)(R')$, —$(CH_2)_{1-4}C(CH_3)_2N(R)(R')$, —OR', —$(CH_2)_{1-4}$ OR', —$NR(CH_2)_{1-4}N(R)(R')$, —$NR(CH_2)_{1-4}SO_2R'$, —$NR(CH_2)_{1-4}C(O)OR'$, or —$NR(CH_2)_{1-4}COR'$, or: two occurrences of $R^6$, taken together with the atoms to which they are bound, form an optionally substituted 3-6-membered saturated, partially unsaturated, or fully unsaturated ring.

3. The compound according to claim 1, wherein
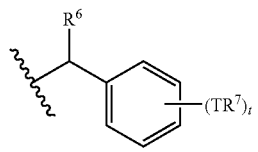
is selected from any of the following:
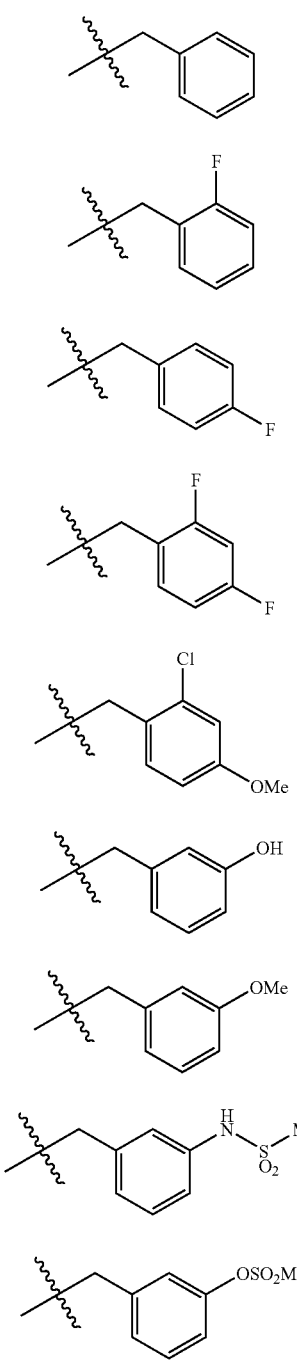
a
b
c
d
e
f
g
h
i
-continued
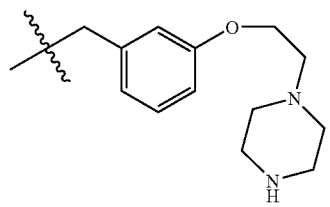
j
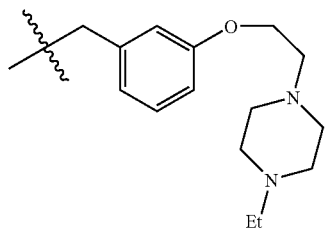
k
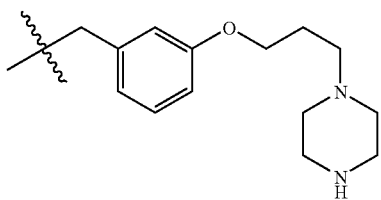
l
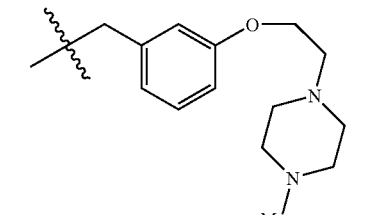
m
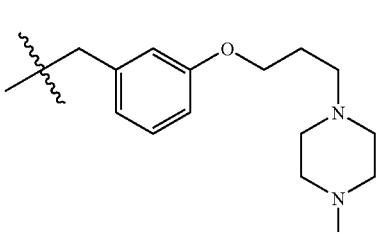
n
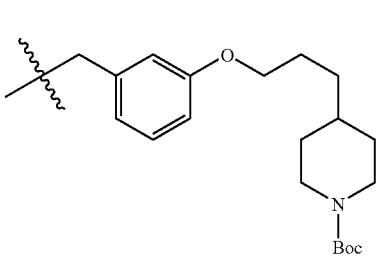
o
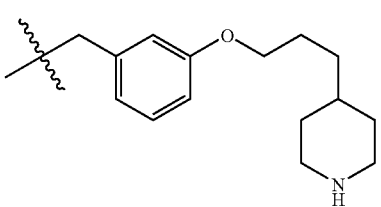
p -continued
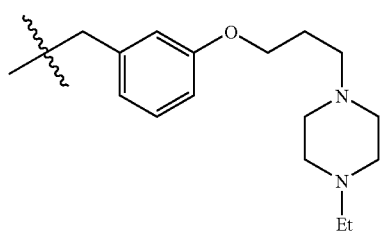 q
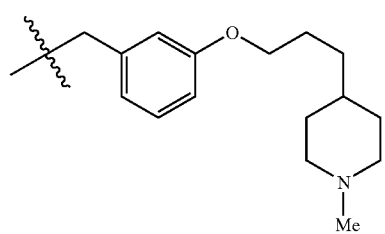 r
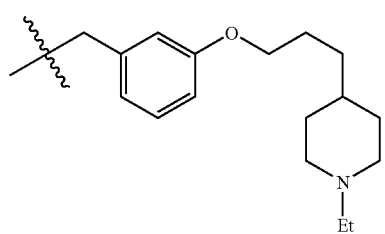 s
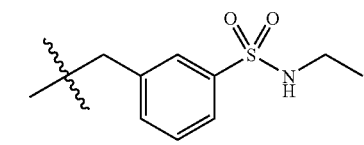 t
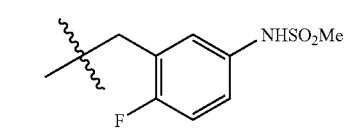 u
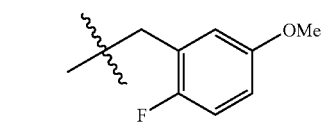 v
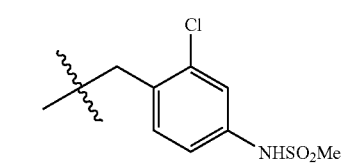 w
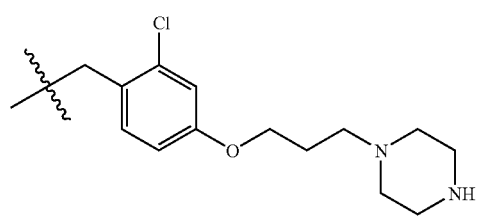 x
-continued
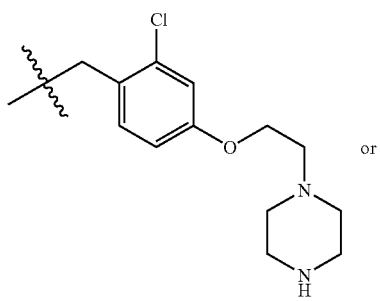 y
or
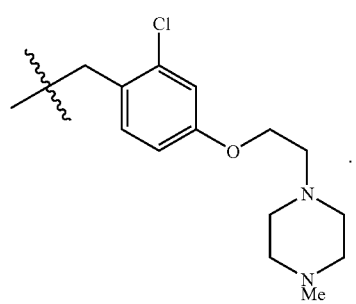 z
4. A compound selected from the group consisting of:
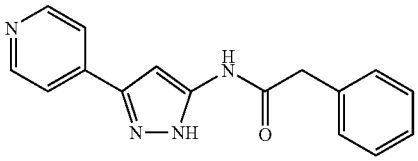 I-1
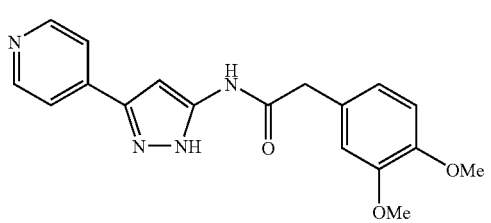 I-2
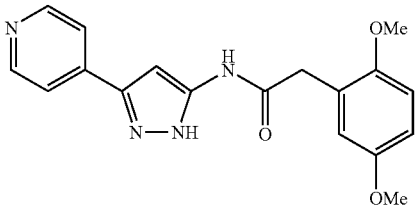 I-3
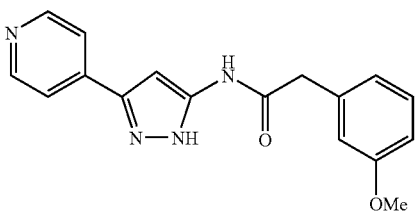 I-4

-continued
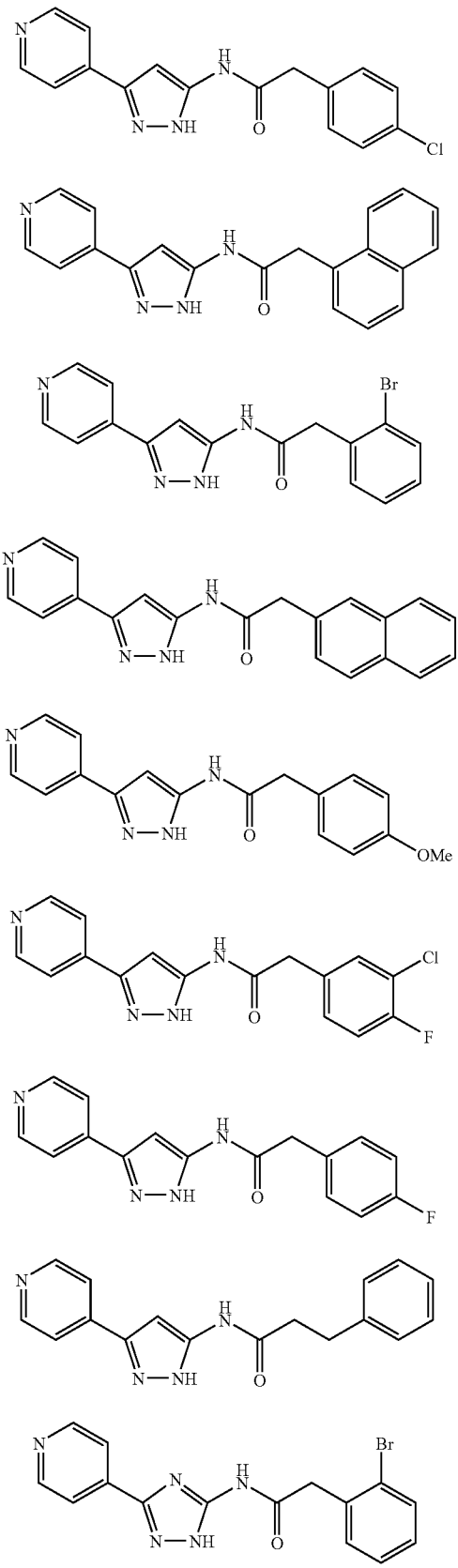
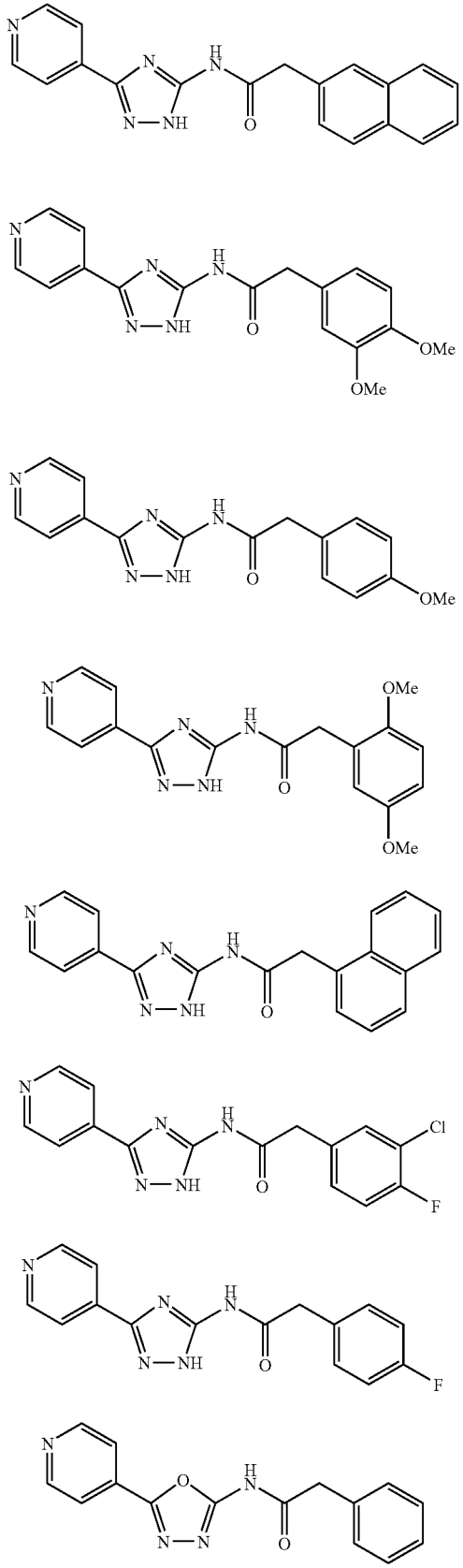

-continued

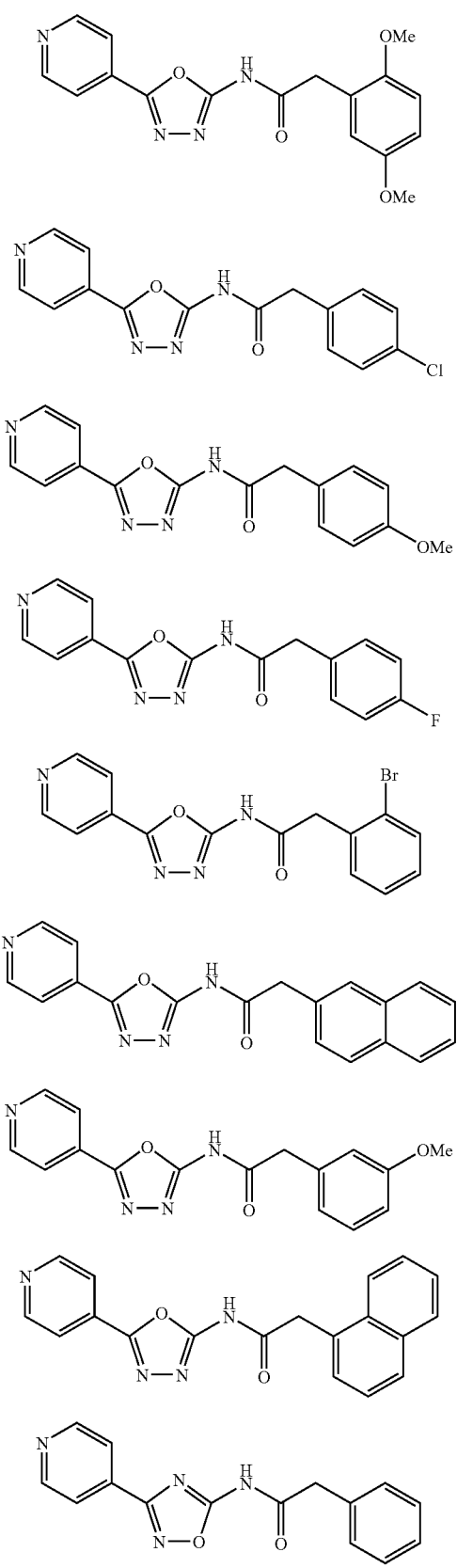

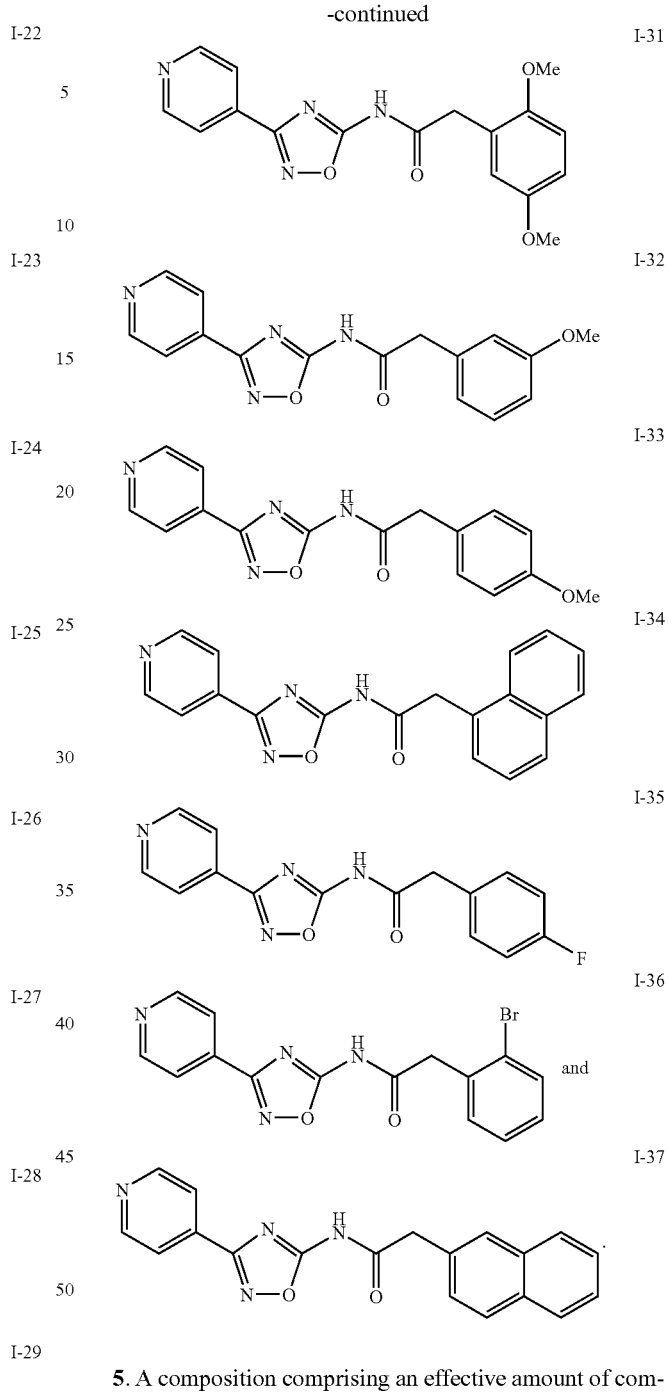

5. A composition comprising an effective amount of compound of claim 1, and a pharmaceutically acceptable carrier, adjuvant, or vehicle.

6. A method of treating or lessening the severity of a disease condition or disorder selected from allergy, asthma, diabetes, or glaucoma comprising the step of administering to said patient a compound of claim 1 or a composition of claim 5.

7. The method of claim 6, wherein disease, condition, or disorder is allergy, asthma, or diabetes.

8. The method of claim 6, wherein disease, condition, or disorder is glaucoma.

* * * * *